United States Patent
Reilly

(10) Patent No.: US 8,962,574 B2
(45) Date of Patent: Feb. 24, 2015

(54) METHOD FOR TREATING OR PREVENTING THROMBOSIS USING DABIGATRAN ETEXILATE OR A SALT THEREOF WITH IMPROVED SAFETY PROFILE OVER CONVENTIONAL WARFARIN THERAPY

(75) Inventor: Paul Anthony Reilly, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 47 days.

(21) Appl. No.: 13/128,459

(22) PCT Filed: Nov. 10, 2009

(86) PCT No.: PCT/EP2009/064873
§ 371 (c)(1),
(2), (4) Date: Jun. 16, 2011

(87) PCT Pub. No.: WO2010/055021
PCT Pub. Date: May 20, 2010

(65) Prior Publication Data
US 2011/0269703 A1  Nov. 3, 2011

Related U.S. Application Data

(60) Provisional application No. 61/237,552, filed on Aug. 27, 2009, provisional application No. 61/113,404, filed on Nov. 11, 2008.

(51) Int. Cl.
*A61K 31/4365* (2006.01)
*A61K 31/44* (2006.01)
*A61K 31/60* (2006.01)
*A61P 7/02* (2006.01)
*A61K 31/4439* (2006.01)

(52) U.S. Cl.
CPC ................................. *A61K 31/4439* (2013.01)

USPC ....... 514/26; 514/13.7; 514/161; 514/211.09; 514/225.2; 514/236.2; 514/46; 514/301; 514/305; 514/315; 514/338; 424/133.1; 424/94.5; 424/569

(58) Field of Classification Search
CPC .................................................. A61K 31/4439
USPC ............. 424/133.1, 94.5, 569; 514/13.7, 161, 514/211.09, 225.2, 236.2, 26, 262.1, 301, 514/305, 338, 46
See application file for complete search history.

(56) References Cited

U.S. PATENT DOCUMENTS

| | | |
|---|---|---|
| 4,145,308 A | 3/1979 | Simoneau et al. |
| 4,191,741 A | 3/1980 | Hudson et al. |

(Continued)

FOREIGN PATENT DOCUMENTS

| | | |
|---|---|---|
| DE | 102005020002 A1 | 11/2006 |
| DE | 102005025728 A1 | 12/2006 |

(Continued)

OTHER PUBLICATIONS

Ezekowitz et al. (American Heart Journal, May 2009, pp. 805-810.*

(Continued)

*Primary Examiner* — Savitha Rao
(74) *Attorney, Agent, or Firm* — Michael P. Morris; Wendy A. Petka

(57) ABSTRACT

A method for preventing stroke in a patient suffering from atrial fibrillation, wherein the patient has at least one risk factor for major bleeding events, the method comprising administering to the patient 110 mg b.i.d. of dabigatran etexilate, optionally in the form of a pharmaceutically acceptable salt thereof.

18 Claims, 3 Drawing Sheets

(56) References Cited

U.S. PATENT DOCUMENTS

| | | | |
|---|---|---|---|
| 5,277,820 | A | 1/1994 | Ash |
| 5,422,121 | A | 6/1995 | Lehmann et al. |
| 6,087,380 | A | 7/2000 | Hauel et al. |
| 6,358,960 | B1 | 3/2002 | Senokuchi et al. |
| 6,620,439 | B1 | 9/2003 | Mehta |
| 7,880,016 | B2 | 2/2011 | Zerban et al. |
| 7,932,273 | B2 | 4/2011 | Schmid et al. |
| 8,119,810 | B2 | 2/2012 | Broeder et al. |
| 8,354,543 | B2 | 1/2013 | Zerban et al. |
| 8,378,113 | B2 | 2/2013 | Heddesheimer et al. |
| 8,399,678 | B2 | 3/2013 | Gnad et al. |
| 8,471,033 | B2 | 6/2013 | Filser et al. |
| 2003/0181488 | A1 | 9/2003 | Brauns |
| 2003/0211168 | A1 | 11/2003 | Lynenskjold et al. |
| 2006/0183779 | A1 | 8/2006 | Brauns et al. |
| 2006/0222640 | A1 | 10/2006 | Reilly et al. |
| 2008/0039391 | A1 | 2/2008 | Clemens et al. |
| 2008/0119523 | A1 | 5/2008 | Schmid et al. |
| 2008/0200514 | A1 | 8/2008 | Clemens et al. |
| 2010/0087488 | A1 | 4/2010 | Pop et al. |
| 2010/0099882 | A1 | 4/2010 | Broeder et al. |
| 2010/0144796 | A1 | 6/2010 | Pop et al. |
| 2010/0184729 | A1 | 7/2010 | Reilly et al. |
| 2010/0210845 | A1 | 8/2010 | Zerban et al. |
| 2010/0322869 | A1 | 12/2010 | Reilly |
| 2010/0322870 | A1 | 12/2010 | Reilly |
| 2011/0015129 | A1 | 1/2011 | Clemens et al. |
| 2011/0118471 | A1 | 5/2011 | Filser et al. |
| 2011/0123635 | A1 | 5/2011 | Radtke |
| 2011/0129538 | A1 | 6/2011 | Landerer et al. |
| 2011/0190352 | A1 | 8/2011 | Feuring |
| 2011/0251160 | A1 | 10/2011 | Reilly |
| 2011/0269799 | A1 | 11/2011 | Reilly |
| 2011/0275824 | A1 | 11/2011 | Gnad et al. |
| 2011/0295018 | A1 | 12/2011 | Heddesheimer et al. |
| 2011/0301201 | A1 | 12/2011 | Reilly |
| 2011/0306640 | A1 | 12/2011 | Van Ryn et al. |
| 2012/0040384 | A1 | 2/2012 | Stangier |
| 2012/0116089 | A1 | 5/2012 | Broeder et al. |
| 2012/0276206 | A1 | 11/2012 | Maier |
| 2012/0277269 | A1 | 11/2012 | Reilly |
| 2012/0282187 | A1 | 11/2012 | Reilly |
| 2013/0251810 | A1 | 9/2013 | Landerer et al. |
| 2013/0251811 | A1 | 9/2013 | Radtke |

FOREIGN PATENT DOCUMENTS

| | | | |
|---|---|---|---|
| WO | 2006045756 | A1 | 5/2006 |
| WO | 2007040560 | A2 | 4/2007 |
| WO | 2008009639 | A2 | 1/2008 |
| WO | 2008009640 | A1 | 1/2008 |
| WO | 2008095928 | A1 | 8/2008 |
| WO | 2009118321 | A1 | 10/2009 |
| WO | 2009118322 | A1 | 10/2009 |
| WO | 2009153214 | A1 | 12/2009 |
| WO | 2009153215 | A1 | 12/2009 |
| WO | 2010007016 | A1 | 1/2010 |
| WO | 2010055021 | A1 | 5/2010 |
| WO | 2010055022 | A1 | 5/2010 |
| WO | 2010055023 | A1 | 5/2010 |
| WO | 2011061080 | A1 | 5/2011 |

OTHER PUBLICATIONS

Ezekowitz et al. (American Journal of Cardiology, Nov. 1, 2007, pp. 1419-1426).*
Atrial fibrillation: Treatment and drugs, Mayoclinic, dated Jun. 30, 2008. Downloaded from the internet on Feb. 29, 2012, URL: http://www.mayoclinic.com/health/atrial-fibrillation/DS00291/DSECTION=treatments-and-drugs.*
Pawar et al. (HKMJ vol. 4, Dec. 1998, pp. 415-418).*
Baetz et al., "Dabigatran Etexilate: An Oral Direct Thrombin Inhibitor for Prophylaxis and Treatment of Thromboembolic Diseases", Pharmacotherapy, Boston, US. vol. 28, No. 11, Part 1, Nov. 1, 2008, pp. 1354-1373, XP008100341.
Benz, Kerstin, et al; Hemofilttration of Recombinant Hirudin by Different Hemodialyzer Membranes: Implications for Clinical Use; Clinical Journal American Society of Nephrology (2007) vol. 2 pp. 470-476.
Conolly S.J. et al., "Dabigatran versus Warfarin in Patients with Atrial Fibrillation", The New England Journ. of Med., Sep. 17, 2009, vol. 361, No. 12, pp. 1139-1151. XP00564147.
Cooper, G.M., et al; A Randomized Clinical Trial of Activated Charcoal for the Routine Management of Oral Drug Overdose; QJM (2005) vol. 98 pp. 655-660.
Crowther, M. A., et al; Managing Bleeding in Anticoagulated Patients with a focus on Novel Therapeutic Agents; Journal of Thrombosis and Haemostasis (2009) vol. 7 pp. 107-110.
Guss, D.A.; Activated Charcoal—The First Line Agent in Cases of Overdose; Western Journal of Medicine (1989) vol. 151, No. 1 p. 63.
Ieko, Masahiro; Drug Evaluation: Dabigatran Etexilate, a Thrombin Inhibitor for the Prevention of Venous Thromboembolism and Stroke; Current Opinion in Investigation Drugs Scientific (2007) vol. 8, No. 9 pp. 758-768.
International Search Report and Written Opinion for PCT/2009/064874 mailed Feb. 3, 2010.
International Search Report and Written Opinion for PCT/EP2009/064873 mailed Feb. 3, 2010.
International Search Report and Written Opinion for PCT/EP2009/064875 mailed Feb. 3, 2010.
Kawasaki, Chiyo, I., et al; How Tightly Can a Drug Be Bound to a Protein and Still Be Removable by Charcoal Hemoperfusion in Overdose Cases? Clinical Toxicology (2005) vol. 43, No. 2 pp. 95-99.
Mohammed, Haris Umer Usman., et al; "Advancement in Antithrombotics for Stroke", Journ. of Interventional Cardiac Electrophysiology, Kluwer Academic Publishers, vol. 22, No. 2, Apr. 17, 2008, pp. 129-137, XP019607075.
Nagarakanti, Rangadham, et al; Long-term Open Label Extension of the Prevention of Embolix and Thrombotic Events on Dabigatran in Atrial Fibrillation (Petro-Ex Study) Database Biosis [online] Biosciences Inforation Service, Philadelphia, US., Oct. 2008, vol. 118, No. 18, Suppl. 2, p. S922, 18XP002564148.
Nishio, Hitoshi., et al., "New Therapeutic Option for Thromboembolism—Dabigatran Etexilate", Expert Opinion on Pharmacotherapy, Oct. 2008, vol. 9, No. 14, pp. 2509-2517.
Pond, Susan, M; A Review of the Pharmacokinetics and Efficacy of Emesis, Gastric Lavage and Single and Repeated Doses of Charcoal in Overdose Patients: New Concepts and Developments in Toxicology (1986) vol. 12 pp. 315-328.
Prescott, L. F., et al; Treatment of Quinine Overdose with Repeated Oral Charcoal; British Journal of Clinical Pharmacology (1989) vol. 27, No. 1 pp. 95-97.
Rote Liste Fachinformationen: "Drug Information on Pradaxa" http://www.fachinfo.de/data/fi/jsearch?wirkstoff; Aug. 1, 2010.
Stangier, Joachim, et al; The Pharmacokinetics and Tolerability of Dabigatran Etexilate, A New Oral Direct Thrombin Inhibitor, in Healthy Male Subjects; British Journal of Clinical Pharmacology (2007) vol. 64, No. 3 pp. 292-303.
U.S. Appl. No. 12/934,828, filed Nov. 23, 2010, Maier, Johann-Georg.
U.S. Appl. No. 13/543,080, filed Jul. 6, 2012, Reilly, Paul Anthony.
U.S. Appl. No. 13/548,423, filed Jul. 13, 2012, Reilly, Paul Anthony.
U.S. Appl. No. 60/310,341, filed Aug. 6, 2001, Hauel, Norbert.
International Search Report for PCT/EP2009/057266 mailed Apr. 8, 2009.
Hauel, Norbert H., et al; Structure-Based Design of Novel Potent Nonpeptide Thrombin Inhibitors; Journal of Medicinal Chemistry (2002) vol. 45, No. 9 pp. 1757-1766.
International Search Report for PCT/EP2009/057265 mailed Aug. 6, 2009.
International Search Report for PCT/EP2010/066 mailed Feb. 28, 2011.
Zacharski, L.R.; Clinical trials with anticoagulant drugs in patients with cancer; Journal of Cancer Research and Clinical Oncology 1990, vol. 116 part 2 p. 908.

(56) References Cited

OTHER PUBLICATIONS

Connolly, et al., "Challenges of Establishing New Antithrombotic Therapies in Atrial Fibrillation", Circulation, 2007, vol. 116, p. 449-455.
Eriksson, et al., "dabigatran Extexilate" Nature Review Drug Discovery, 2008, vol. 7, p. 557-558.
Bauer, "Targeted inhibition of coagulation: oral agents show promise in phase III trials", Journal of Thrombosis and Haemostasis, 2007, vol. 5, No. 11, p. 2175-2177.
Lopes, et al., "Antithrombotic therapy in atrial fibrillation: guidelines translated for the clinician", J. Thromb, Thrombolysis, 2008, vol. 26, p. 167-174.

* cited by examiner

Figure 1. Thromboembolic and Major Bleeding Events in PETRO and PETRO-Ex studies

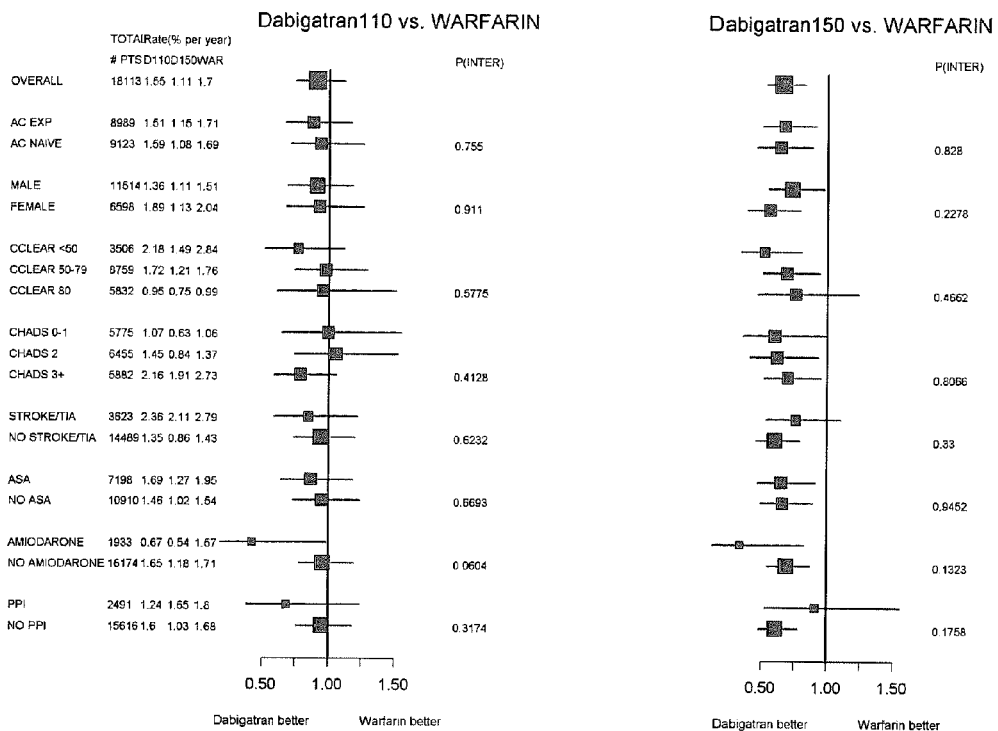

Each whisker represents the relative risk (dabigatran:warfarin) and the 95% CI for the outcome of stroke or systemic embolism. Abbreviations: AC EXP=anticoagulation experienced; AC Naive = anticoagulation naïve, defined as less than 61 days of use of Vitamin K antagonist therapy ever; CCLEAR = calculated creatinine clearance using the Cockcroft-Galt method; ASA, amiodarone and PPI refer to baseline use of aspirin, amiodarone or a proton pump inhibitor; and P(inter) is the p-value for the interaction.

FIG. 3

METHOD FOR TREATING OR PREVENTING THROMBOSIS USING DABIGATRAN ETEXILATE OR A SALT THEREOF WITH IMPROVED SAFETY PROFILE OVER CONVENTIONAL WARFARIN THERAPY

This application is the national phase entry under 35 U.S.C. §371 of International Application No. PCT/EP2009/064873, filed Nov. 10, 2009, which claims priority to U.S. Provisional Patent Applications No. 61/113,404, filed Nov. 11, 2008 and 61/237,552, filed Aug. 27, 2009, the contents of which are hereby incorporated by reference in their entireties.

FIELD OF THE INVENTION

The present invention relates to methods of using dabigatran etexilate, optionally in the form of a pharmaceutically acceptable salt thereof, that provide advantages over conventional warfarin and other vitamin K antagonist therapies.

BACKGROUND OF THE INVENTION

Atrial fibrillation (AF) is a common cardiac arrhythmia which increases the risk of stroke, other embolic events, and death. AF affects 2.2 million people in the United States, and 4.5 million in the EU. AF is the most common heart rhythm disorder and is a major risk factor for stroke. The incidence of AF increases with age and nearly 6% of individuals over the age of 65 are affected. Patients with AF are at risk of developing clots due to the rapid irregular beating of the heart. AF increases the chance of stroke five-fold. As the consequences of stroke can be devastating, a primary aim of therapy is to decrease the risk of arterial thrombus formation and thromboembolism. Long-term anticoagulation therapy with vitamin K antagonists (VKAs or coumadins) such as warfarin is recommended for individuals with AF who are considered at moderate to high risk of stroke. These stroke, thrombosis, or embolism risk factors include age over 65 years, a history of a previous stroke or transient ischemic attack, hypertension, diabetes, or heart failure. Further risk factors for stroke are known to the physician and also defined hereinbelow.

VKAs, such as warfarin, reduce the risk of stroke by 64% compared to control, but increase the risk of hemorrhage. Hart R G, Pearce L A, and Aguilar M I, *Meta-analysis: Antithrombotic therapy to prevent stroke in patients who have nonvalvular atrial fibrillation*, Ann of Intern Med., 2007, 146:857-867. When compared to placebo, warfarin also reduces mortality. Therefore, warfarin is recommended for patients with atrial fibrillation at risk for stroke. Fuster V, et al., *ACC/AHA/ESC 2006 guidelines for the management of patients with atrial fibrillation—executive summary: a report of the American College of Cardiology/American Heart Association Task Force on Practice Guidelines and the European Society of Cardiology Committee for Practice Guidelines (Writing Committee to Revise the 2001 Guidelines for the Management of patients Patient with Arial Fibrillation)*, J Am Coll Cardiol, 2006, 48:854-906.

VKAs, such as warfarin, are cumbersome to use due to multiple diet and drug interactions and require frequent laboratory monitoring. Therefore they are often not used, and discontinuation rates are high. Birman-Deych E, Radford M J, Nilasena D S, Gage B F, *Use and Effectiveness of Warfarin in Medicare Beneficiaries with Atrial Fibrillation*, Stroke, 2006, 37:1070-1074; Hylek E M, Evans-Molina C, Shea C, Henault L E, Regan S, *Major Hemorrhage and Tolerability of Warfarin in the First Year of Therapy Among Elderly Patients with Atrial Fibrillation*, Circulation, 2007, 115:2689-2696. Furthermore, even when on warfarin, many patients have inadequate anticoagulation. Connolly S J, Pogue J, Eikelboom J, Flaker G, Commerford P, Franzosi M G, Healey J S, Yusuf S, ACTIVE W Investigators. *Benefit of oral anticoagulant over antiplatelet therapy in atrial fibrillation depends on the quality of international normalized ratio control achieved by centers and countries as measured by time in therapeutic range*, Circulation, 2008, 118 (20):2029-37. Accordingly, although warfarin reduces stroke in atrial fibrillation, it increases hemorrhage and is difficult to use. Thus, although anticoagulation therapy with warfarin has been shown to significantly reduce the incidence of stroke, only half of eligible patients are estimated to receive appropriate treatment due to a variety of barriers in administration and use of VKAs. Therefore, there is a need for new effective, safe, and convenient anticoagulants.

All of the patents, patents applications, and documents cited herein are each hereby incorporated by reference in their entireties.

SUMMARY OF THE INVENTION

Methods for preventing or treating thrombosis in a patient in need thereof are provided while preventing an adverse bleeding event. The methods involve administering an effective amount of dabigatran etexilate, optionally in the form of a pharmaceutically acceptable salt thereof, to the patient where the patient has not undergone surgery within 10 days, 42 days, 50 days, or 90 days. Such compositions when administered in accordance with the methods of the invention are effective for the prevention or treatment of thrombosis. At the same time the methods of the invention provide an advantage over currently used methods in that adverse bleeding events are prevented in the patients.

In another embodiment, the methods find use in preventing stroke in a patient with atrial fibrillation. The methods involve administering an effective amount of dabigatran etexilate, optionally in the form of a pharmaceutically acceptable salt thereof, to the patient. The patient is at a reduced risk for an adverse bleeding event particularly when compared to treatment with warfarin.

The methods of the invention comprise administering pharmaceutical compositions comprising a therapeutically effective amount of dabigatran etexilate, optionally in the form of a pharmaceutically acceptable salt thereof. Additionally the pharmaceutical compositions may comprise a pharmaceutically acceptable carrier. In general, a daily dosage of from 100 mg to 600 mg of dabigatran etexilate, optionally in the form of a pharmaceutically acceptable salt thereof, provides a beneficial balance between thromboembolic relief and low bleeding rates. In particular, a unit dose of 100 mg to 200 mg of dabigatran etexilate twice daily (b.i.d.) represents a beneficial balance between thromboembolic relief and low bleeding rates.

The present inventors have found that in patients with risk factors for major bleeding events a unit dose of 100 mg to 120 mg, preferably 110 mg, of dabigatran etexilate twice daily (b.i.d.) represents a beneficial balance between thromboembolic relief and low bleeding rates.

More specifically, the invention relates to a method for preventing stroke in a patient suffering from atrial fibrillation, wherein the patient has at least one risk factor for major bleeding events, the method comprising administering to the patient 110 mg b.i.d. of dabigatran etexilate, optionally in the form of a pharmaceutically acceptable salt thereof. This method can also be used to prevent stroke in a patient suffering from atrial fibrillation, wherein the patient has at least two risk factors for major bleeding events. Risk factors for major bleeding events include, but are not limited to, a patient (a) being the age of 75 years or greater, (b) having history of earlier bleeding events, and (c) having a reduced creatinine clearance less than 80 mL/min or less than 50 mL/min.

Another object of the present invention relates to the use of dabigatran etexilate, optionally in the form of a pharmaceutically acceptable salt thereof, for the manufacture of a medicament for the prevention of stroke in patients suffering from atrial fibrillation wherein the patient has at least one risk factor for major bleeding events, wherein the use comprises the b.i.d. administration of 110 mg dabigatran etexilate, optionally in the form of a pharmaceutically acceptable salt thereof. The use of dabigatran etexilate, optionally in the form of a pharmaceutically acceptable salt thereof, for the manufacture of a medicament for the prevention of stroke in patients suffering from atrial fibrillation may also be used in a patient that has at least two risk factors for major bleeding events. As mentioned above, risk factors for major bleeding events include, but are not limited to, a patient (a) being the age of 75 years or greater, (b) having history of earlier bleeding events, and (c) having a reduced creatinine clearance less than 80 mL/min or less than 50 mL/min.

Similarly, the invention relates to a medicament for the prevention of stroke in a patient suffering from atrial fibrillation wherein the patient has at least one risk factor for major bleeding events, the medicament comprising 110 mg of dabigatran etexilate, optionally in the form of a pharmaceutically acceptable salt thereof. The 110 mg dosage may also be adapted for b.i.d. administration. This medicament may also be used in a patient that has at least two risk factors for major bleeding events. Risk factors for major bleeding events include, but are not limited to, a patient (a) being the age of 75 years or greater, (b) having history of earlier bleeding events, and (c) having a reduced creatinine clearance less than 80 mL/min or less than 50 mL/min.

In yet another embodiment, the invention relates to a method for preventing or treating thrombosis in a patient in need thereof and reducing the risk of a major bleeding event, hemorrhagic stroke, intracranial stroke, or mortality compared to conventional warfarin therapy, the method comprising administering 110 mg b.i.d. of dabigatran etexilate, optionally in the form of a pharmaceutically acceptable salt thereof, wherein the patient has not undergone surgery within 10 days, 42 days, 50 days, or 90 days. Additionally, this method may be used in a patient that has a creatinine clearance of more than 30 mL/min. In contrast, it may be important to discontinue administration of dabigatran etexilate or salt thereof if the patient has a creatinine clearance of 30 mL/min or less.

In one embodiment of the above-defined method, the major bleeding event is a life-threatening bleeding event. In further embodiment, this method may be used in a patient that is at increased risk for hemorrhage than the general population. In yet another embodiment of this method, a patient has at least one risk factor for major bleeding events. Also included is a medicament for treatment of thrombosis in a patient in need thereof and reducing the risk of a major bleeding event, hemorrhagic stroke, intracranial stroke, or mortality according to the methods above. The methods just described may further comprise monitoring the patient for bleeding adverse events, which includes: (a) administering to the patient dabigatran etexilate, optionally in the form of a pharmaceutically acceptable salt thereof, 110 mg b.i.d.; (b) monitoring the patient for bleeding adverse events; and (c) administering to the patient dabigatran etexilate, optionally in the form of a pharmaceutically acceptable salt thereof, 150 mg b.i.d. if the monitoring determines no bleeding adverse events. The monitoring step may occur over a period of at least 3 months, at least 6 months, or at least 1 year.

The present invention also relates to a method for preventing stroke in a patient having at least one stroke, thrombosis, or embolism risk factor and reducing the risk of a major bleeding event or mortality compared to conventional warfarin therapy, the method comprising administering 110 mg b.i.d. of dabigatran etexilate, optionally in the form of a pharmaceutically acceptable salt thereof, to the patient. Risk factors for stroke are known to the physician and are also defined hereinbelow.

In one embodiment of this method, the major bleeding event is a life-threatening bleeding event. In another embodiment of this method, the patient has atrial fibrillation. The methods just described may further comprise monitoring the patient for bleeding adverse events, which includes: (a) administering to the patient dabigatran etexilate, optionally in the form of a pharmaceutically acceptable salt thereof, 110 mg b.i.d.; (b) monitoring the patient for bleeding adverse events; and (c) administering to the patient dabigatran etexilate, optionally in the form of a pharmaceutically acceptable salt thereof, 150 mg b.i.d. if the monitoring determines no risk for a major bleeding event. The monitoring step may occur over a period of at least 3 months, at least 6 months, or at least 1 year.

Another object of the present invention includes a method for preventing or treating thrombosis in a patient in need thereof, the method comprising administering 110 mg b.i.d. of dabigatran etexilate, optionally in the form of pharmaceutically acceptable salt thereof, wherein the patient is not suitable for conventional warfarin therapy.

Also included in the present invention is a method for preventing or treating thrombosis in a patient in need thereof, the method comprising administering 110 mg b.i.d. of dabigatran etexilate, optionally in the form of a pharmaceutically acceptable salt thereof, wherein conventional warfarin therapy is contraindicated.

According to any one of the methods described above, the dabigatran etexilate, optionally in the form of a pharmaceutically acceptable salt thereof, may be administered for at least 3 months, at least 6 months, at least 9 months, at least 12 months, or at least 48 months.

Another embodiment of the invention relates to a method for lowering the risk of an adverse event in a patient having a condition being treated with warfarin, the method comprising: (a) discontinuing administration of warfarin to the patient; and (b) administering to the patient 110 mg b.i.d. of dabigatran etexilate, optionally in the form of a pharmaceutically acceptable salt thereof. In one embodiment, the condition is SPAF. In another embodiment, the adverse event is bleeding.

A further embodiment of the invention relates to a method for preventing stroke in a patient with atrial fibrillation, the method comprising administering 110 mg b.i.d. of dabigatran etexilate, optionally in the form of a pharmaceutically acceptable salt thereof, to the patient and modifying the administration as necessary to maintain plasma levels of dabigatran in the patient between about 20 ng/mL to about 180 ng/mL, wherein the patient is at a reduced risk for a major bleeding event when compared to conventional warfarin therapy. Plasma levels of dabigatran may further be between about 43 ng/mL to about 143 ng/mL, between about 50 ng/mL to about 120 ng/mL, between about 50 ng/mL to about 70 ng/mL or between about 60 ng/mL to about 100 ng/mL and the plasma levels of dabigatran may be determined using a standardized lyophilized dabigatran method. In one embodiment of this method, the major bleeding event is a life-threatening bleeding event.

The invention also relates to a method for preventing or treating thrombosis and preventing a major bleeding event, hemorrhagic stroke, intracranial stroke, or mortality in a patient in need thereof, the method comprising administering 110 mg b.i.d. of dabigatran etexilate, optionally in the form of a pharmaceutically acceptable salt thereof, to the patient and modifying the administration as necessary to maintain plasma levels of dabigatran in the patient between about 20 ng/mL to about 180 ng/mL, wherein the patient is at a reduced risk for a major bleeding event when compared to conventional warfarin therapy and wherein the patient has not undergone surgery within 10 days, 42 days, 50 days, or 90 days. Plasma levels of dabigatran may further be between about 43 ng/mL to about 143 ng/mL, between about 50 ng/mL to about 120 ng/mL, between about 50 ng/mL to about 70 ng/mL or between about 60 ng/mL to about 100 ng/mL and the plasma levels of dabigatran may be determined using a standardized lyophilized dabigatran method. In one embodiment of this method, the major bleeding event is a life-threatening bleeding event.

Another object of the present invention relates to the use of dabigatran etexilate, optionally in the form of a pharmaceutically acceptable salt thereof, for making a medicament for treating atrial fibrillation, wherein dabigatran etexilate, optionally in the form of a pharmaceutically acceptable salt thereof, is administered at 110 mg b.i.d. dabigatran etexilate, optionally in the form of a pharmaceutically acceptable salt thereof. According to this method, the dabigatran etexilate, optionally in the form of a pharmaceutically acceptable salt thereof, may be administered for at least: 3 months, 6 months, 9 months, 12 months, 24 months, 48 months, or 10 years.

In another embodiment, the invention relates to a dose unit comprising 110 mg of dabigatran etexilate, optionally in the form of a pharmaceutically acceptable salt thereof, for the treatment of atrial fibrillation. The invention also includes a medicament for the treatment of atrial fibrillation bioequivalent within 80% to 125% with respect to this dose unit under a b.i.d. treatment regimen. The invention also includes a kit comprising: (a) a medicament for the treatment of atrial fibrillation comprising solid dose units of 110 mg of dabigatran etexilate, optionally in the form of a pharmaceutically acceptable salt thereof; and (b) instructions to use one solid dose twice daily.

One embodiment of the invention is a medicament for preventing stroke in patients with atrial fibrillation at risk of stroke comprising a fixed doses of dabigatran which is equivalent to 110 mg dabigatran etexilate b.i.d. wherein events of stroke or systemic embolism as primary outcome are not inferior to unblinded adjusted warfarin treatment within a median follow-up of 2.0 years stroke or systemic embolism is not inferior to conventional warfarin therapy, preferably where the primary outcome is 1.70% per year on warfarin versus 1.55% per year on dabigatran (relative risk 0.91, 95% confidence interval 0.75 to 1.12; p [non-inferiority] <0.001).

Another embodiment of the invention is a medicament for stroke in patients with atrial fibrillation at risk of stroke comprising a fixed doses of dabigatran which is equivalent to 110 mg dabigatran etexilate b.i.d. with reduced rates of major hemorrhage as primary outcome compared to unblinded adjusted warfarin treatment within a median follow-up of 2.0 years, preferably with rates of major hemorrhage of 3.46% per year on warfarin versus 2.74% per year on dabigatran etexilate 110 mg (p=0.002).

Yet another embodiment of the invention is a medicament for treatment of atrial fibrillation at risk of stroke comprising a fixed doses of dabigatran which is equivalent to 110 mg dabigatran etexilate b.i.d. with reduced mortality as primary outcome compared to unblinded adjusted warfarin treatment within a median follow-up of 2.0 years, preferably with mortality rates of 4.13% per year on warfarin versus 3.74% per year on dabigatran 110 mg (p<0.12).

The invention also includes the above medicaments, comprising a dabigatran prodrug that is bioequivalent within the range of 80% to 125% to dabigatran etexilate 110 mg b.i.d. or a dabigatran prodrug that is bioequivalent within the range of 80% to 125% with an amount of dabigatran etexilate methanesulfonate corresponding to 110 mg dabigatran etexilate applied in a b.i.d. treatment regimen.

The invention also includes the above methods, wherein the dabigatran etexilate, optionally in the form of a pharmaceutically acceptable salt thereof, is co-administered with an antiplatelet agent, for example, wherein the antiplatelet agent is aspirin and is administered at less than or equal to 100 mg per day. Preferably the antiplatelet agent is aspirin, dipyridamole, clopidogrel, abciximab, eptifibatide, tirofiban, epoprostenol, streptokinase, or a plasminogen activator.

The invention further includes the above methods, wherein the dabigatran etexilate, optionally in the form of a pharmaceutically acceptable salt thereof, is co-administered with an antiarrhythmic agent, for example, wherein the antiarrhythmic agent is a potassium channel blocker, sodium channel blocker, beta blocker, or calcium channel blocker. Preferably the antiarrhythmic agent is quinidine, procainamide, disopyramide, lidocaine, mexiletine, tocainide, phenytoin, flecainide, encainide, propafenone, moracizine, propranolol, esmolol, metoprolol, timolol, atenolol, miodarone, sotalol, dofetilide, ibutilide, erapamil, diltiazem, amiodarone, bretylium, verapamil, diltiazem, adenosine, or digoxin.

For purposes of clarity, all the methods described herein are also useful for treating thrombosis, which in turn are useful for treating thromboembolism, systemic thromboembolism, or systemic embolism, and the like.

BRIEF DESCRIPTION OF THE DRAWINGS

FIG. 3: Effects of dabigatran on the primary outcome, compared to warfarin, according to important patient subgroups.

DETAILED DESCRIPTION OF THE INVENTION

Figure 1:
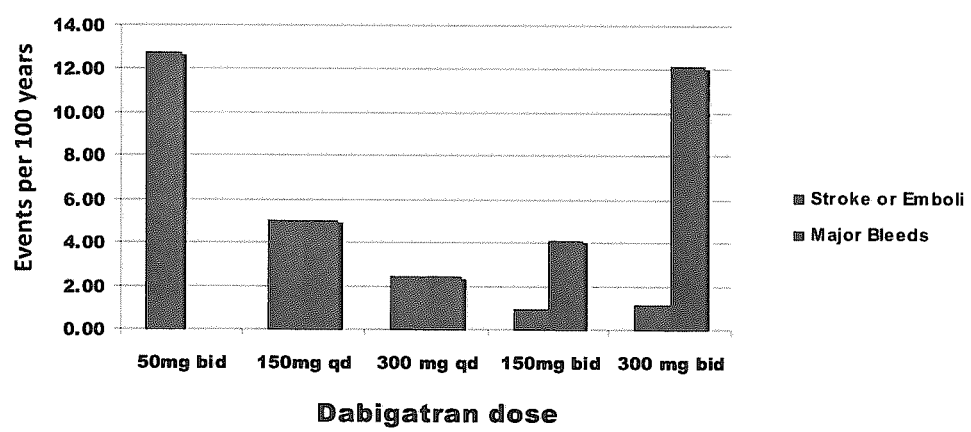
FIG. 1: Thromboembolic and Major Bleeding Events in PETRO and PETRO-Ex Studies. Subject−years=sum (date of study termination−date of randomization+1) of all randomized subject/365.25.

Dabigatran etexilate is a compound of Formula (I)

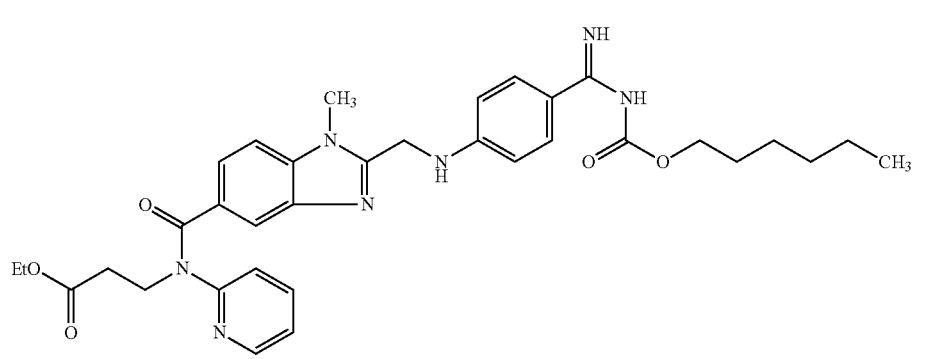

(I)

and is an oral direct thrombin inhibitor useful in the prophylaxis of thromboembolism in patients undergoing total knee or hip replacement and also suitable for the prevention of stroke, in particular in patients with atrial fibrillation. Other indications also exist, see, e.g., U.S. Patent Application Pub. Nos. 2008/0015176; 2008/0039391; and 2008/0200514. The compound of Formula (I) is already known from WO 98/37075 (corresponding to U.S. Pat. Nos. 6,087,380; 6,469,039; 6,414,008; and 6,710,055), in which compounds with a thrombin-inhibiting and thrombin time-prolonging activity are disclosed, under the name 1-methyl-2-[N-[4-(N-n-hexyloxycarbonylamidino)phenyl]aminomethyl]benzimidazol-5-ylcarboxylic acid-N-(2-pyridyl)-N-(2-ethoxycarbonylethyl)amides. Dabigatran etexilate is a double prodrug of dabigatran, the compound of Formula (II)

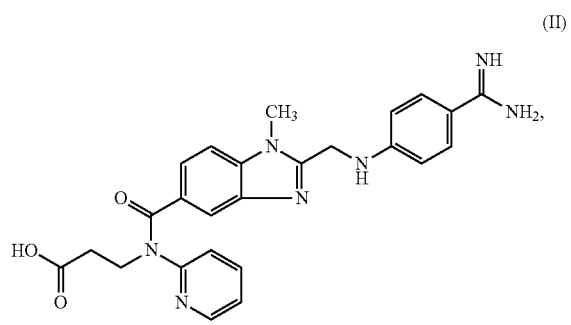 [SMILES: Cn1c(CNc2ccc(C(=N)N)cc2)nc2cc(C(=O)N(CCC(=O)O)c3ccccn3)ccc21]

(II)

i.e., dabigatran etexilate is only converted into the compound which is actually effective, namely dabigatran, in the body. Dabigatran etexilate is preferably administered in the form of its methanesulfonate salt, although also the salts of dabigatran etexilate with other pharmaceutically acceptable acids are encompassed in the context of the present invention. See, e.g., U.S. Patent Application Pub. No. 2006/0183779.

Dabigatran is a new oral direct thrombin inhibitor which has advantages over warfarin and other VKAs. Dabigatran etexilate is an oral pro-drug rapidly converted by a serum esterase to dabigatran, a potent direct competitive inhibitor of thrombin. Its serum half-life is 12 to 17 hours, and it does not need regular monitoring. Stangier J, Clinical pharmacokinetics and pharmacodynamics of the oral direct thrombin inhibitor dabigatran etexilate, Clin Pharmacokinet, 2008, 47:285-295. Dabigatran has been evaluated in a pilot trial in atrial fibrillation and in prevention of venous thromboembolism after orthopedic surgery, where doses of 150 mg twice daily (b.i.d.) and 220 mg once daily were promising. Ezekowitz M D, et al., *Dabigatran with or without concomitant aspirin compared with warfarin alone in patients with nonvalvular atrial fibrillation (PETRO study)*, Am. J. Cardiol., 2007, 100: 1419-1426; Eriksson B I, et al., *Dabigatran etexilate versus enoxaparin for prevention of venous thromboembolism after total hip replacement: a randomized, double-blind, non-inferiority trial*, Lancet 2007, 370:949-56. The PETRO study is described below. The RELY Clinical Trial, described below, was a large randomized trial, comparing dabigatran 110 mg twice daily and 150 mg twice daily with warfarin.

As noted above, management of warfarin therapy is complex, and failure to adequately monitor patients is associated with risk. Warfarin has a narrow therapeutic window, a slow onset and offset of action, and is associated with an unpredictable dose response. It also interacts with many common foods, drugs and alcohol which alter its therapeutic effect, putting patients at risk of either a bleeding or thrombotic event. Therefore, warfarin therapy requires careful individualized dosing and frequent monitoring. The significant limitations of VKAs have created a need for an oral anticoagulant with a rapid onset of action, minimal drug interactions, and a predictable anticoagulation effect that needs no monitoring. The oral direct thrombin inhibitor, dabigatran etexilate fulfils these requirements. The onset of anticoagulant effect is within one hour of dosing, and is administered once or twice daily, without monitoring.

Dabigatran etexilate exhibits no food interactions. Oral bioavailability is low, averaging 6.5%. It is metabolized by tissue esterases to the active compound, dabigatran. Peak levels are seen within 2-3 hours of oral administration. The plasma half life is 12-17 hours after multiple doses. It has a low potential for drug-drug interactions as this prodrug is not metabolized by and does not induce or inhibit cytochrome P-450 drug metabolizing enzymes. Dabigatran is moderately bound (25-35%) to plasma proteins. Steady-state is reached within 2-3 days with a twice daily regimen. Approximately 80% of dabigatran is cleared unchanged by the kidney. The remainder undergoes conjugation with glucuronic acid to form acylglucuronides which are excreted primarily in the bile.

Dabigatran binds directly and reversibly to thrombin at its active site and prevents cleavage of fibrinogen to fibrin to block the final step of the coagulation cascade and thrombus formation. Dabigatran, unlike heparin, also inhibits thrombin that is bound to fibrin or fibrin degradation products. Dabigatran exhibits dose dependent prolongation of activated partial thromboplastin time (aPTT), ecarin clotting time, and thrombin clotting time. The anticoagulant effects parallel plasma concentrations. As with other direct thrombin inhibitors, the correlation between aPTT and dabigatran plasma concentrations is non-linear with considerable variability and a flattened response at higher plasma concentrations. The ecarin clotting time and thrombin clotting time have steeper linear correlations with dabigatran concentrations and lower variability.

Dabigatran has been approved in Europe for the prevention of thromboembolism after hip and knee surgery. In such indication dabigatran etexilate is applied for a limited time period where the patient is at risk for thromboembolism, after which time the application is terminated. Such treatment periods are limited and generally ranging from 10 days up to a maximum of 42 days.

Because of the safety and efficacy of dabigatran, it is particularly useful in therapeutic methods to prevent or avoid an adverse bleeding event. In one embodiment of the invention, a method is provided for preventing or treating thrombosis in a patient in need thereof wherein the patient has not undergone surgery, particularly, hip and knee surgery, for at least about 50 days, at least about 60 days, at least about 70 days or longer. The method involves administering a daily dosage of from 100 mg to 600 mg of dabigatran etexilate or a pharmaceutically acceptable salt thereof.

In another embodiment, the methods find use in preventing thrombosis, embolism, or stroke in a patient with atrial fibrillation (AF). The method comprises administering a daily dosage of an effective amount of dabigatran etexilate, optionally in the form of a pharmaceutically acceptable salt thereof, to the patient wherein the patient is at a reduced risk for an adverse bleeding event, particularly when compared to treatment of the patient with warfarin.

Prior to the publication of the study results of PETRO, different posologies and different possible dosages for the prevention of stroke in patients with AF were mentioned in the art. However, a physician searching for an appropriate treatment for a specific patient suffering from AF was not able to decide which dosage would be appropriate. This was particularly difficult if the physician had to decide on the appropriate medication for a patient that suffered from AF and at least one risk factor for major bleeding events as defined herein below.

Thus, an important objective of the instant invention is to provide for a method for the prevention of stroke in a patient suffering from atrial fibrillation, wherein the patient is further characterized by at least one risk factor for major bleeding events.

Patients suffering from AF may have additional risk factors for thrombosis, embolism, or stroke. These stroke, thrombosis, or embolism risk factors are known to the physician and defined hereinbelow.

However, the method according to the invention focuses on the prevention of thrombosis, embolism, or stroke, preferably stroke, in patients that are characterized by risk factors for major bleeding events. One important risk factor for major bleeding events is the age of at least 75 years. Another risk factor for major bleeding events may include a history of earlier bleeding events and the like. Furthermore, a reduced creatinine clearance less than 80 mL/min, preferably less than 50 mL/min, most preferably less than 30 mL/min, could possibly amount to a risk factor for major bleeding events. Further risk factors for major bleeding events are known to the physician and also defined hereinbelow.

The method comprises administering an effective amount of dabigatran etexilate, optionally in the form of a pharmaceutically acceptable salt thereof, to the patient.

Treatment of these patients at risk for major bleeding events is particularly useful as the patient is at a reduced risk for a major bleeding event when compared to treatment with warfarin.

AF is a chronic condition, which is presently not curable but can only be relieved. Patients suffering from AF require to be treated with dabigatran etexilate lifelong. Thus, there is a need for determining a dosage range suitable for long-term treatment using dabigatran etexilate for patients suffering from AF. Specifically, there exists a need for determining a dosage range and treatment scheme (posology), which balances thromboembolic prevention and minimizes risk factors, especially bleeding, in particular in patients with an identified risk factor for major bleeding events. In the treatment of AF, the suitability of a patient having risk factors, e.g., stroke and bleeding, is determined by a skilled physician. In one embodiment, the physician identifies a patient having AF and an additional risk factor for treatment with dabigatran etexilate.

A pharmaceutically effective amount or therapeutically effective amount for the methods and uses described herein, including preventing thrombosis, embolism, or stroke in a patient with AF (with or without risk factors for major bleeding) and/or who has not undergone surgery for a specified period, generally within 10 days, 42 days, 50 days, or 90 days, is a daily dosage of from 100 mg to 600 mg, including 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 375 mg, 390 mg, 400 mg, 425 mg, 450 mg, 475 mg, 500 mg, 525 mg, 550 mg, 575 mg, and 600 mg of dabigatran etexilate, optionally in the form of or a pharmaceutically acceptable salt thereof. In preferred embodiments, dabigatran etexilate, optionally in the form of or a pharmaceutically acceptable salt thereof, is administered at a daily dosage of from 75 mg b.i.d. to a daily dosage of 300 mg b.i.d., including a daily dosage of from 100 mg b.i.d., 110 mg b.i.d., 115 mg b.i.d., 120 mg b.i.d., 125 mg b.i.d., 130 mg b.i.d., 135 mg b.i.d., 140 mg b.i.d., 145 mg b.i.d., 150 mg b.i.d., 155 mg b.i.d., 160 mg b.i.d., 170 mg b.i.d., 180 mg b.i.d., 190 mg b.i.d., 200 mg b.i.d., 210 mg b.i.d., 220 b.i.d., 230 mg b.i.d., and any such dose falling between 75 mg b.i.d. to 300 mg b.i.d. In one proffered embodiment, dabigatran etexilate, optionally in the form of or a pharmaceutically acceptable salt thereof, is administered at a daily dosage of 110 mg b.i.d.

A further objective of the present invention is to provide a dosage regimen for dabigatran etexilate, which meets the above requirements and is suitable for a treatment term of 3 months and more. Due to the chronic nature of the disease, treatment periods are even more extended. It is a further objective of the present invention to identify such a dosage regimen, which is suitable for patients of different age, gender, and weight and physical constitution.

Dabigatran can be made into pharmaceutical formulations, see, e.g., U.S. Patent Application Pub. No. 2005/0038077; U.S. Patent Application Pub. Nos. 2005/0095293; 2005/0107438; 2006/0183779; and 2008/0069873. In addition, dabigatran can be administered with other active ingredients, see, e.g., U.S. Patent Application Pub. Nos. 2006/0222640; 2009/0048173; and 2009/0075949.

DEFINITION OF TERMS AND CONVENTIONS USED

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

The terms "minor hemorrhage" and "minor bleeding event" means a bleeding event that does not fulfill the criteria for a major bleeding event.

The terms "major hemorrhage", "major bleeding event", and "major bleeds" mean a reduction in hemoglobin level of at least 2.0 g/L or transfusion of at least 2 units of blood or symptomatic bleeding in a critical area or organ.

The terms "life-threatening bleeding" and "life-threatening bleeding event" mean a subset of major bleeding event that includes fatal bleeding, symptomatic intracranial bleeding, bleeding with hemoglobin decrease of more than 5.0 g/L, or requiring transfusion of more than 4 units of blood or requiring inotropic agents or necessitating surgery.

The term "warfarin" means an anticoagulant that acts by inhibiting vitamin K-dependent coagulation factors and is sold under the brand names Coumadin, Jantoven, Marevan, and Waran. Chemically, it is 3-(α-acetonylbenzyl)4-hydroxycoumarin and is a racemic mixture of the R- and S-enantiomers. Warfarin is a synthetic derivative of coumarin, a chemical found naturally in many plants. Warfarin decreases blood coagulation by inhibiting vitamin K epoxide reductase, an enzyme that recycles oxidized vitamin K to its reduced form.

The term "conventional warfarin therapy" relates to the amount of warfarin administered to a patient according to the ACC/AHA/ESC Practice Guidelines (Fuster et al., JACC, Vol. 48, No. 4, Aug. 15, 2006, 854-906; see, e.g., page 859, Class 1 recommendation, points 3 and 4), incorporated herein by reference. The RELY Clinical Trial used conventional warfarin therapy as the comparator.

The term "dabigatran etexilate" means a compound of Formula (I) including its pharmaceutically acceptable salts. The single dosage amount of dabigatran etexilate in any salt form in mg refers to the free base, i.e., to the free base of Formula (I). The dose amount of prodrug dabigatran etexilate is based on the weight of its free base.

The term "dabigatran" is the compound of Formula (II) in its free base form.

The term "AF" means atrial fibrillation, a cardiac arrhythmia.

The term "SPAF" means stroke prevention in atrial fibrillation.

The term "non-valvular atrial fibrillation" means AF in the absence of rheumatic mitral stenosis or a prosthetic heart valve.

The terms "thrombotic events" and "thromboembolic events" mean an occurrence of thromboembolies or stroke. "Thrombosis" is the formation of a blood clot (thrombus) inside a blood vessel, obstructing the flow of blood through the circulatory system. If a clot breaks free, an embolus is formed. "Thromboembolism" is the formation in the blood vessel of a clot that breaks loose and is carried by the blood stream to plug another vessel. The clot may plug a vessel in the lungs (pulmonary embolism), brain (stroke), gastrointestinal tract, kidneys, or leg.

The terms "non-CNS systemic embolism" or "SE" means that a piece of blood clot that breaks off from a clot, often in the left atrial chamber of the heart, flows through the systemic circulation and blocks a pat of the circulation other than the brain (when it blocks brain circulation it's a stroke).

The term "hemorrhagic stroke" means a bleed inside the brain.

The terms "subarachnoid hemorrhage" or "subarachnoid bleed" mean a bleeding into the subarachnoid space, the area between the arachnoid membrane and the pia mater surrounding the brain.

The terms "subdural hemorrhage" or "subdural bleed" mean a bleeding within the inner meningeal layer of the dura, the outer protective covering of the brain, surrounding the brain.

The term "intracranial hemorrhage" or "ICH" means a hemorrhagic stroke including subdural bleed plus subarachnoid bleed. Hemorrhagic stroke is bleed inside the brain and subdural hemorrhage and subarachnoid hemorrhage are on the surface of the brain but outside the brain and ICH is a composite of these different bleeds.

The term "International Normalized Ratio" or "INR" means the ratio of a patient's prothrombin time to a normal (control) sample, raised to the power of the ISI value for the analytical system used:

$$INR = \left(\frac{PT_{test}}{PT_{normal}}\right)^{ISI}.$$

The prothrombin time (PT) is the time it takes plasma to clot after addition of tissue factor (obtained from animals). This measures the quality of the extrinsic pathway (as well as the common pathway) of coagulation. The speed of the extrinsic pathway is greatly affected by levels of factor VII in the body. Factor VII has a short half-life and its synthesis requires vitamin K. The prothrombin time can be prolonged as a result of deficiencies in vitamin K, which can be caused by warfarin, malabsorption, or lack of intestinal colonization by bacteria (such as in newborns). In addition, poor factor VII synthesis (due to liver disease) or increased consumption (in disseminated intravascular coagulation) may prolong the PT. A high INR level such as INR=5 indicates that there is a high chance of bleeding, whereas if the INR=0.5 then there is a high chance of having a clot. Normal range for a healthy person is 0.9-1.3, and for people on warfarin therapy, 2.0-3.0, although the target INR may be higher in particular situations, such as for those with a mechanical heart valve, or bridging warfarin with a low-molecular weight heparin (such as enoxaparin) perioperatively.

The term "stroke, thrombosis, or embolism risk factors" means the risk factors that are known to statistically increase the risk of thrombosis, embolism, or stroke. These risk factors include: AF, having a history of stroke; having a history of a transient ischemic attack; having a history of a thromboembolic event; having left ventricular dysfunction; having an age of at least 65 years and having high blood pressure; having an age of at least 65 years and having diabetes; having an age of at least 65 years and having coronary artery disease; and, having an age of at least 65 years and having peripheral artery disease. Accordingly, generally stroke, thrombosis, or embolism risk factors include age; heredity; gender; prior stroke, transient ischemic attack, or heart attack; high blood pressure; cigarette smoking; diabetes mellitus; carotid or other artery disease; atrial fibrillation or other heart disease; sickle cell disease; high blood cholesterol; diets high in saturated fat, trans fat, cholesterol, and sodium; and physical inactivity and obesity.

The National Stroke Association (US) indicates that one is at a "high risk of stroke" if they have at least 3 of the following risk factors: a blood pressure at 140/90 or higher; a cholesterol level of 240 or higher; has diabetes; is a smoker; suffers from atrial fibrillation; is overweight; does not exercise; or, has a history of stroke in their family.

The National Stroke Association (US) indicates that one is at a "moderate risk of stroke" if they have 4-6 of the following: a blood pressure of 120-139/80-89; a cholesterol level of 200-239; is borderline for diabetes; is trying to quit smoking; is not aware of having an irregular heartbeat; is slightly overweight; exercises sometimes; and is not sure of a family history of stroke.

The National Stroke Association (US) indicates that one is at a "low risk of stroke" if they have 6-8 of the following: a blood pressure of 120/80 or lower; a cholesterol of 200 or lower; does not have diabetes; is not a smoker; does not have an irregular heartbeat; is at a healthy weight; exercises regularly; and does not have a history of stroke in their family.

The term "risk factors for major bleeding events" means various risk factors that are known to statistically increase the risk of a patient having a major bleeding event. Risk factors for major bleeding events are known to the physician working in the field. For safety reasons, the existence of risk factors for major bleeding events need to be determined by the physician in every patient. As an example, the risk factors for major bleeding events can be grouped into demographics (age, gender, and nursing facility residence). As an example, patients being at the age of 75 years or greater could be considered a risk factor for major bleeds. These risk factors can also include alcohol/drug abuse, concomitant diseases (anemia, cancer, stroke, transient ischemic attacks, MI, hypertension, heart failure/cardiomyopathy, ischemic heart disease, diabetes, hepatic failure, or peptic ulcer disease) and concomitant risks for injury (risk for falls, cognitive impairment, or surgery during index hospitalization). Risk factors for major bleeding events are also present in patients having a history of earlier bleeding events or in patients having a reduced creatinine clearance, for instance, less than 80 mL/min, less than 50 mL/min, or less than 30 mL/min.

The term "b.i.d." means that the daily dosage is administered in two separate administrations, which are timely separated by at least 4 hours, preferably at least 6 hours and more preferably at least 8 hours. Consequently, a dosage of 110 mg b.i.d. means a daily dosage of 220 mg, which is administered twice daily at a single dose of 110 mg.

The dosages referred to herein are based on the amount of dabigatran etexilate free base (i.e., the compound depicted in Formula (I)). If dabigatran etexilate is administered in form of one of its pharmaceutically acceptable salts the amount of the salt that is used is to be calculated from the indicated dosage. As an example, if dabigatran etexilate is administered in form of its methanesulfonate salt a dosage of 110 mg equals an amount of 126.83 mg of dabigatran etexilate methanesulfonate.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety. Most preferred according to the invention is the methanesulfonic acid addition salt of dabigatran etexilate which is also referred to herein as dabigatran etexilate methanesulfonate.

The term "prevent" means to keep from happening or continuing and relates to a statistical reduction in the risk of an event occurring. "Preventing" is synonymous with "reducing the risk" or "demonstrating a lower incidence" of an event occurring. Reducing the risk or demonstrating a lower incidence means that there is a statistical reduction or lowering in occurrence of the event by at least 1% or greater. Preferably, this reduction is by 7% or greater, 10% or greater, 20% or greater, 26% or greater, 34% or greater, 50% or greater, 64% or greater and 74% or greater. These reductions include confidence intervals greater than 50%, greater than 75%, greater than 80%, greater than 90%, greater than 95%, greater than 98% and greater than 99%. Confidence intervals of greater than 95% are preferred.

The methods of the invention provide a safe and therapeutically effective amount of dabigatran etexilate, optionally in the form of a pharmaceutically acceptable salt thereof. By "safe and therapeutically effective amount" is intended an amount of dabigatran etexilate, optionally in the form of a pharmaceutically acceptable salt thereof, that when administered in accordance with the invention is free from major complications, such as an adverse bleeding event, that cannot be medically managed, and that provides for objective improvement in patients by preventing or treating thrombosis. It is recognized that the therapeutically effective amount may vary from patient to patient depending upon age, weight, severity of symptoms, general health, physical condition, and the like. Typically, a therapeutically effective amount of dabigatran etexilate, optionally in the form of a pharmaceutically acceptable salt thereof, is a daily dosage of about 100 mg to about 600 mg, more preferably a therapeutically effective amount of dabigatran etexilate, optionally in the form of a pharmaceutically acceptable salt thereof, is a twice daily oral dosage of 75 mg to about 200 mg, and most preferably a therapeutically effective amount of dabigatran etexilate, optionally in the form of a pharmaceutically acceptable salt thereof, is a twice daily oral dosage of 110 mg or 150 mg. Patients having at least one risk factor for major bleeding events as described and defined hereinbefore are preferably treated with a dosage of 110 mg b.i.d. dabigatran etexilate, possibly in the form of one of its pharmaceutically acceptable acid addition salts.

A "therapeutically effective amount" can also be determined based on plasma levels of dabigatran, optionally in the form of a pharmaceutically acceptable salt thereof, in the patient. Typically, the plasma level will be in the range of: about 20 ng/mL to about 180 ng/mL, about 43 ng/mL to about 143 ng/mL, about 50 ng/mL to about 120 ng/mL, about 50 ng/mL to about 70 ng/mL or 60 ng/mL to about 100 ng/mL.

Due to its double prodrug nature, a "bioequivalent therapeutically effective amount" an amount of dabigatran etexilate means any formulation of dabigatran etexilate as free base or pharmaceutically acceptable salts of dabigatran etexilate or any derivative of a dabigatran prodrug of Formula (III), infra, as free base or any of its pharmaceutically acceptable salts, that generates a dabigatran plasma level comparable to the level obtained using dabigatran etexilate as comparator drug. Depending on national or regional regulatory standards, bioequivalence is demonstrated if the plasma level of the drug or formulation in question is within a defined percentage range. U.S. FDA and the EU EMEA require a 80% to 125% range to prove bioequivalence and are established by the agencies' respective regulations.

Determining Dabigatran Plasma Levels

Although clinical monitoring of dabigatran is generally not required, a reliable laboratory method to measure the pharmacodynamic effects of dabigatran is useful for some of the methods of the invention. Such an analytical method for determining dabigatran plasma levels could be used not only to monitor the kinetics of the drug activity in the body but also to adjust dosing and posology of the drug, which could be useful to avoid overdosing and analyze the pharmacodynamic effects of dabigatran etexilate.

One such method involves a lyophilized form of dabigatran that can be used as a calibrator in the assays for the determination of pharmacodynamic effects of dabigatran etexilate, specifically a method for the quantitative determination of dabigatran in blood samples. The method involves the determination of the clotting time that is initiated by purified human thrombin. Thus, for measuring the dabigatran plasma concentration, an aliquot of the test plasma sample is diluted with physiological saline, coagulation is then initiated by adding a constant amount of highly purified human thrombin in the a-form, and the coagulation time measured is directly proportional to the concentration of dabigatran in the tested sample. For purposes of this application, this method will be known as the "standardized lyophilized dabigatran method".

In order to be able to determine the concentration of dabigatran in the investigated blood sample according to this method, a calibration curve should be generated that makes a correlation of the coagulation time with the concentration of dabigatran in standard samples. The generation of such a calibration curve would use multiple dabigatran standards or calibrators of a defined concentration. Such dabigatran standards would be stable, so that the amount of dabigatran will be constant when stored at −20° C. or above, and easily used in the method to ensure that a reliable calibration curve can be readily established.

Dabigatran etexilate tends to crystallize in different polymorphic forms, is hygroscopic (thereby leading also to the formation of different hydrated forms), and is sparingly soluble in water. Accordingly, a lyophilized form of dabigatran of Formula (II) is useful as a calibrating substance for dabigatran. To make the lyophilized form of dabigatran, a defined amount of dabigatran drug substance is dissolved in aqueous acid and diluted in water and the resulting solution is used as a stock solution for the preparation of the different dabigatran calibrator samples. An appropriate selection of different aliquots of the dabigatran stock solution are added to human anticoagulated plasma that has been obtained from healthy volunteer donors (human pool plasma) according to methods known in the art to produce solutions with different dabigatran concentrations. Specified volumes of these different solutions are transferred into suitable tubes and lyophilized to complete dryness in an appropriate freeze drying device and stable lyophilized forms of dabigatran of known concentration suitable for generating a calibration curve are obtained. This lyophilized dabigatran is easily reconstituted and, therefore, useful as a calibrator for the determination of the dabigatran concentration in unknown blood samples based on the coagulation time observed after coagulation is initiated by adding the same amount of highly purified human thrombin in the α-form to the unknown sample. Such standard samples of lyophilized dabigatran and highly purified human thrombin in the a-form can be packaged in a kit. Quality control to determine the accuracy of the assay could be determined by periodically testing a sample with a known quantity of dabigatran.

The pH of the aqueous acidic solution used for the dissolution of dabigatran is preferably $\leq 3$, more preferably $\leq 2$.

Although many acids could be used, the acids are preferably hydrochloric acid, hydrobromic acid, sulfuric acid, phosphoric acid, methanesulfonic acid, acetic acid, fumaric acid, citric acid, tartaric acid, or maleic acid, particularly hydrochloric acid. The human anticoagulated plasma can be obtained according to any of the methods known by one of skill in the art and is preferably human citrated anticoagulated plasma or human EDTA anticoagulated plasma.

An example of the procedure follows. The chronometric coagulation assays were performed with two Behnk CL4 ball coagulometers (Behnk Elektronik, Germany) used according to the operating instructions. The Hemoclot Thrombin Inhibitor Assay was used (HYPHEN BioMed, France). The following 2 reagents from the kit are used: (1) normal pooled citrated plasma, lyophilized (Reagent 1); and (2) highly purified human calcium thrombin (α-form) stabilized with additives and lyophilized (Reagent 2).

The performance of the coagulation test with dabigatran plasma samples was evaluated with the analytical method evaluation program "Analyse-it" for Excel, Version 2.09, Analyse-it Software, Ltd. PO Box 103, Leeds LS27 7WZ England, United Kingdom.

Step A. Preparation of Lyophilized Dabigatran Calibrators 5.55 mg of dabigatran of Formula (II) is dissolved in 200 μL 1M HCl and diluted in ultrapure water to give a final volume of 50 mL. This stock solution of 111 μg/mL dabigatran is stored at 4° C. Human citrated plasma from healthy volunteer donors (human pool plasma) is used for the preparation of dabigatran calibrators. Aliquots of the dabigatran stock solution are diluted in human citrated pool plasma to lead to solutions with the different final dabigatran concentrations 100, 500, 1500, and 2000 nM dabigatran. Aliquots of 500 μL volume of the human pool plasma with 100, 500, 1500, or 2000 nM dabigatran are transferred into polypropylene tubes and lyophilized using a Christ Alpha RVC, Typ CMC-2 vacuum centrifuge to complete dryness for approximately 8 hours (pressure: 3 mbar). Lyophilized dabigatran calibrators are stored at −20° C.

Step B. Preparation of Standards (Calibration Curve)

Add 0.5 mL of ultrapure water to each vial of the dabigatran calibrators of 0 (blank), 100, 500, 1500, and 2000 nM dabigatran obtained according to Step A, mix gently, and incubate for 15 minutes at normal room temperature. Calibrator plasma must be diluted 1:8, e.g., 100 μL standard and 700 μL phys. NaCl. Pipette 50 μL of calibrator sample into the coagulometer cuvettes (duplicate determination). Measure each calibrator as described in Step E.

Step C. Preparation of Reagents

Calculate the necessary volume of reagents for the daily amount of samples. Dissolve each vial of Reagent 1 and Reagent 2 in 1 mL ultrapure water; mix gently, and incubate for 15 minutes at normal room temperature. The stability of prepared reagents is as follows: Reagent 1: +18° C. to +25° C. (24 h); +2° C. to +8° C. (48 h); and −20° C. (2 months); and Reagent 2: +18° C. to +25° C. (24 h); +2° C. to +8° C. (48 h); and −20° C. (2 months).

Step D. Plasma Sample Collection and Preparation

Collect blood sample on 0.109 M trisodium citrate anticoagulant (ratio 9:1 blood/citrate). Decant plasma supernatant following a 20 minute centrifugation at 2.5 g. The stability of plasma is as follows: +18° C. to +25° C. (8 h); +2° C. to +8° C. (24 h); $\leq$−20° C. (up to 6 months). Thaw samples at +37° C. for maximum of 45 minutes. Keep thawed samples at normal room temperature. Sample plasma must be diluted 1:8, e.g., 100 μL sample and 700 μL phys. NaCl.

Step E. Measurement Procedure

The following measurement procedure is conducted first with the calibrator samples prepared according to Step B. After preparation of the calibration curve, the plasma samples prepared according to Step D are measured accordingly.

Mix samples (calibrator or plasma) by gentle agitation. Transfer 50 μL plasma sample each (obtained according to Step B or D) into 2 cuvettes (each sample is measured in duplicate). Pipette 100 μL of Reagent 1 (preincubated at 37° C.) into a cuvette. At the same time, start a 1 minute incubation period by activating a timer. By the end of the incubation time, add 100 μL of Reagent 2 (preincubated at 37° C.) to the cuvette. A stopwatch is started. The time until the ball's rotation in the Behnk CL4 ball coagulometer stops is measured (clotting time [sec]). The instrument's software calculates the mean clotting time [sec] of the duplicate measurement. The result of both determinations and the mean clotting time is documented on paper print.

Step F. Generation of Calibration Curve

The coagulation times obtained by measuring the calibrator samples with 0 (blank sample), 100, 500, 1500, and 2000 nM (wider concentration range and additional concentrations, e.g., 250 nM are possible) are plotted versus the dabigatran calibrator concentration in a scatter plot using a spreadsheet program (MS Excel or the like). A calibration curve is established by simple linear regression analysis. By determination of the coagulation time, the corresponding dabigatran concentration in a plasma sample can be determined directly from the calibration line. With lyophilized dabigatran samples of defined concentrations, e.g. 100, 500, and 1500 nM, a quality control system is available. Quality control sample coagulation time measurement and subsequent determination of the corresponding dabigatran concentration using the calibration curve allows for the determination of assay accuracy. Assay accuracy is assessed by comparison of the known target concentration of the dabigatran quality control sample and the calculated concentration of this quality control sample using the coagulation time and calibration curve.

The dabigatran etexilate, optionally in the form of a pharmaceutically acceptable salt thereof-containing pharmaceutical compositions of the invention will be delivered for a time sufficient to achieve the desired physiological effect, i.e., prevention or treatment of thrombosis. Typically, the pharmaceutical compositions will be delivered as an oral composition twice a day. The compositions may be administered for a defined time or indefinitely.

When administered in accordance with the methods of the invention, dabigatran etexilate, optionally in the form of a pharmaceutically acceptable salt thereof, provides the patient with a safe and therapeutically efficacious method for the prevention or treatment of thrombosis. The dabigatran etexilate, optionally in the form of a pharmaceutically acceptable salt thereof, is able to prevent thrombosis but not result in an adverse bleeding event.

Dabigatran can be made into pharmaceutical formulations, see, e.g., U.S. Patent Application Pub. Nos. 2005/0038077; 2005/0095293; 2005/0107438; 2006/0183779; and 2008/0069873. In addition, dabigatran can be administered with other active ingredients, see, e.g., U.S. Patent Application Pub. Nos. 2006/0222640; 2009/0048173; and 2009/0075949. A pharmaceutically acceptable carrier or diluent that is conventionally used in the art can be used to facilitate the storage, administration, and/or the desired effect of the therapeutic ingredients. A suitable carrier should be stable, i.e., incapable of reacting with other ingredients in the formulation. Such carriers are generally known in the art. A thorough discussion of formulation and selection of pharmaceutically acceptable carriers, stabilizers, and the like can be found in *Remington's Pharmaceutical Sciences* (18$^{th}$ ed.; Mack Pub. Co.: Eaton, Pa., 1990), herein incorporated by reference.

It is further recognized that the dabigatran etexilate or pharmaceutically acceptable salt thereof may be co-administered with an antiplatelet agent. Antiplatelet agents include cyclooxygenase inhibitors such as aspirin; adenosine diphosphate (ADP) receptor inhibitors; phosphodiesterase inhibitors; glycoprotein IIB/IIIA inhibitors; adenosine reuptake inhibitors; and the like. In one embodiment, the antiplatelet agent is aspirin and is administered at less than or equal to 100 mg per day.

The following examples are offered by way of illustration and not by way of limitation.

EXPERIMENTAL

PETRO and PETRO-Ex Study Trial Results

The efficacy and safety of dabigatran etexilate in patients with atrial fibrillation was studied in a phase 2 Prevention of Embolic and Thrombotic Events in Patients With Persistent Atrial Fibrillation (PETRO) study. This was a 12-week dose finding study of dabigatran etexilate, alone or in combination with aspirin (ASA), compared to the standard anticoagulant regimen of warfarin without aspirin in patients with chronic atrial fibrillation. In this study, 502 patients were randomized to warfarin (with INR goal between 2-3) or to dabigatran etexilate (50 mg b.i.d., 150 mg b.i.d., and 300 mg b.i.d.) and three doses of aspirin (0, 81 mg, and 325 mg q.d.). Primary endpoints were bleeding events and changes in D-dimer. There were 2 systemic thromboembolic events in the trial, both in the dabigatran etexilate 50 mg b.i.d. group. Four (6%) major bleeding events occurred in the dabigatran etexilate 300 mg b.i.d. plus ASA groups. Minor bleeding was dose related. Elevated transaminases >3× upper limit of normal (ULN) occurred in 0.9% (4 of 432) of dabigatran etexilate-treated patients. The change in D-dimer levels in patients treated with dabigatran was comparable to warfarin.

To determine the long term safety of dabigatran etexilate, patients who had been randomized to dabigatran etexilate in the PETRO study and had completed treatment without an outcome event were offered placement in the extension, PETRO-Ex study, the data of which are presented here.

Methods

The PETRO-Ex study was conducted in 52 centers in the United States, Denmark, The Netherlands, and Sweden. The protocol was developed by the Steering Committee. The data management and statistical analysis were performed by Boehringer Ingelheim. The statistical analysis plan was developed by the Steering Committee. All authors concurred with the findings.

The primary objective was to evaluate the long term safety and efficacy of dabigatran in patients with atrial fibrillation by determining the incidence of major bleeding events, systemic thromboembolism and liver function test abnormalities.

PETRO-Ex was a long term, extension study of patients randomized to dabigatran in PETRO trial and completed their treatment per protocol. Unlike the PETRO study, which was double blind with respect to dabigatran etexilate dosage, PETRO-Ex was open label. PETRO-Ex began while the PETRO study was ongoing and investigators were initially kept blinded to patient treatment group until PETRO was completed. Unblinding investigators to patient treatment was possible thereafter.

Data were summarized descriptively; no hypothesis was to be tested. Events were analyzed on the basis of the treatment at onset. Incidences were reported as number of patients with events as well as normalized to 100 patient-years on the respective treatment. Event risks were compared between treatments with the help of the risk ratio and its 95% confidence interval (2-sided).

Patients were included if they met all the following criteria: age ≥18 years, previous treatment with dabigatran in the PETRO study and no premature discontinuation of therapy; paroxysmal, persistent, or permanent (chronic) non-rheumatic atrial fibrillation, documented by ECG prior to enrollment in PETRO study; at least one additional risk factor for stroke: hypertension, diabetes, heart failure or left ventricle dysfunction, previous ischemic stroke or transient ischemic attack, age greater than 75 years, and history of coronary artery disease (i.e., previous MI, angina, positive stress test, previous coronary intervention or bypass surgery, or atherosclerotic lesion(s) diagnosed by coronary angiography). Written, informed consent was obtained from all patients.

Patients were excluded if they had: valvular heart disease conferring significantly increased risk of thromboembolic events (e.g., clinically significant mitral stenosis or prosthetic valves), planned cardioversion while patients would be in the study, contraindication to anticoagulant therapy (previous intracranial hemorrhage, GI hemorrhage within previous 3 months, previous severe hemorrhage with warfarin at therapeutic international normalized ratio (INR), regular use of non-steroidal anti-inflammatory drugs, hemorrhagic diathesis) as well as major bleeding within the past 6 months (other than GI hemorrhage) and severe renal impairment with glomerular filtration rate ≤30 mL/min.

Patients who completed PETRO on 50 mg b.i.d. were switched to 150 mg q.d. upon entry in the PETRO-Ex study (N=93 patients). All other patients were initially maintained on the same dabigatran etexilate doses as they received in the PETRO study. Patients who were down titrated to 50 mg q.d. based on a glomerular filtration rate ≤50 mL/min during PETRO were excluded from the long-term trial; patients down-titrated in other dose levels remained on the q.d. treatment at that dose.

Results

Of the 432 patients treated with dabigatran in the PETRO study, 396 completed treatment according to protocol and of these, 361 patients (91%) were enrolled into the PETRO-Ex study. The warfarin arm of the PETRO study was stopped in PETRO-Ex. At entry in PETRO-Ex, patients were a mean of 69.7±8.2 years old, 16.3% female, had a median duration of atrial fibrillation of 4.2 years and a median of 2 stroke risk factors. Use of aspirin in PETRO-Ex was based on the investigator's judgment.

Due to a high frequency of major bleeding events in the 300 mg b.i.d. group (N=162) after several months of extended treatment, with or without aspirin, the Data Safety and Monitoring Board (DSMB) recommended and the Steering Committee agreed that all patients receiving 300 mg b.i.d. be converted to either 300 mg q.d. or 150 mg b.i.d. Similarly, an increased frequency of thromboembolic events in the treatment group receiving a dose of less than 300 mg/day (N=103), led the DSMB to recommend that these patients be up-titrated to either 300 mg q.d. or 150 mg b.i.d. The Steering Committee agreed. Most of the exposure was with dabigatran etexilate 150 mg b.i.d. dose (683.9 patient years) followed by 300 mg q.d. (198.7 patient years), 300 mg b.i.d. (82.0 patient years), 150 mg q.d. (58.5 patient years) and 50 mg b.i.d. (23.5 patient years). The total exposure reflects both trials, PETRO and PETRO-Ex, together.

Thromboembolic events and stroke rate were lowest in the dabigatran etexilate 150 mg b.i.d. (1% per year) and 300 mg b.i.d. (1.2% per year) treatments. During treatment with ≤150 mg/day of dabigatran etexilate, the annualized thromboembolic event rate was over 5.0 per 100 patient years.

Major bleeding events were relevantly higher in the dabigatran etexilate 300 mg b.i.d. compared to the 150 mg b.i.d. and 300 mg q.d. treatments (12.2 vs. 4.2 vs. 2.5% per year). There were 3 major bleeds in the 150 mg q.d. dose. Combined with the data on 50 mg b.i.d., the major bleed rate at doses ≤150 mg/day was 3.7% per year (FIG. 1). The bleeding event rate was significantly higher while on concomitant aspirin (8.5% vs. 3.2% per year; risk ratio 2.70 and CI 1.49-4.86). Five of the major bleeds were fatal; 4 on 150 mg b.i.d. and 1 on 300 mg q.d. Three of these fatal bleeds were intracranial bleeds, one was a GI bleed, and one was an aortic dissection. There was one more intracranial bleed, which was non-fatal.

TABLE 1

Summary of PETRO and PETRO-Ex results

| Dabigatran etexilate dose | 50 mg q.d. | 50 mg b.i.d. | 150 mg q.d. | 300 mg q.d. | 150 mg b.i.d. | 300 mg b.i.d. | Total |
|---|---|---|---|---|---|---|---|
| Subjects treated | 1 | 105 | 103 | 90 | 356 | 162 | 432 |
| Total exposure (Patient years) | 0.05 | 23.51 | 58.52 | 198.68 | 683.88 | 82.01 | 1046.66 |
| Major Bleeds | 0 | 0 | 3 (5.1) | 5 (2.5) | 29 (4.2) | 10 (12.2) | 44(4.2) |
| Of these, without aspirin | 0 | 0 | 3 (6.5) | 3 (2.1) | 18 (3.2) | 4 (6.3) | 26(3.2) |
| with aspirin | 0 | 0 | 0 | 2 (3.6) | 11 (8.7) | 6 (32.7) | 19(8.5) |
| Stroke and Systemic Thromboembolism | 0 | 3 (12.8) | 3 (5.1) | 5 (2.5) | 7 (1.0) | 1 (1.2) | 20(1.9) |
| TIA | 0 | 0 | 0 | 0 | 1 (0.1) | 0 | 1(0.1) |
| MI | 0 | 0 | 0 | 1 (0.5) | 6 (0.9) | 0 | 7(0.7) |
| Other MACE | 0 | 2 (8.5) | 0 | 1 (0.5) | 7 (1.0) | 1 (1.2) | 11(1.1) |
| Adverse Events leading to premature discontinuation | 0 | 5 (21.3) | 8 (13.7) | 19 (9.6) | 67 (9.8) | 21 (25.6) | 120(11.5) |
| ALT or AST >3xULN and Bili >2xULN within 30 days | 0 | 0 | 0 | 1 (0.5) | 3 (0.4) | 0 | 4(0.4) |

TABLE 1-continued

Summary of PETRO and PETRO-Ex results

| Dabigatran etexilate dose | 50 mg q.d. | 50 mg b.i.d. | 150 mg q.d. | 300 mg q.d. | 150 mg b.i.d. | 300 mg b.i.d. | Total |
|---|---|---|---|---|---|---|---|
| ALT or AST >2xULN | 0 | 0 | 2 (3.4) | 3 (1.5) | 21 (3.1) | 4 (4.9) | 30 (2.9) |
| ALT or AST >3xULN | 0 | 0 | 0 | 3 (1.5) | 13 (1.9) | 2 (2.4) | 18 (1.7) |
| ALT or AST >5xULN | 0 | 0 | 0 | 3 (1.5) | 7 (1.0) | 1 (1.2) | 11 (1.1) |

ALT = Alanine Transaminase;
AST = Aspartate Transaminase;
Bili = Total Bilirubin;
CNS = Central Nervous System;
MACE = Major Adverse Cardiac Event;
MI = Myocardial Infarction;
TIA = Transient Ischemic Attack;
ULN = Upper Limit of Normal The data presented in Table 1 are illustrated in FIG. 1.

During the course of the trial, 18 patients (1.7% per year) had elevated liver transaminases, AST or ALT >3xULN, of whom 11 pts (1.1% per year) had transaminases (AST or ALT) >5xULN. There were four patients (0.4% per year) with concomitant bilirubin elevation >2xULN within 30 days of transaminase elevations >3xULN. All of these cases were due to alternative clinical causes.

In all, 9 of the 18 cases with AST or ALT >3xULN, after investigation, had an explanatory clinical diagnosis. In 10 of the 16 on treatment cases, the LFT abnormality resolved with continuation of dabigatran and in 5 cases after stopping of dabigatran; one patient with an on-treatment LFT abnormality died from heart failure and sepsis believed contributory to the abnormalities in liver function. A second patient with unknown outcome had discontinued dabigatran treatment (due to bleeding) three weeks prior to development of liver function abnormalities (off treatment). The details of individual patients with LFT abnormalities and any associated hepatobiliary problems are presented in Table 2.

TABLE 2

INDIVIDUAL PATIENTS WITH LFT ABNORMALITIES

| Age | Sex | ALT/ ULN | AST/ ULN | Alternative Diagnosis | Action taken with Study medicine | Final Outcome/ Comment |
|---|---|---|---|---|---|---|
| 72 | F | >3x | >3x | [Isolated increase] | Discontinued | Recovered |
| 67 | M | — | >5x# | Adenocarcinoma of Pancreas | [Off-treatment] | Fatal |
| 78 | F | >5x | — | [Isolated increase] | Continued | Recovered |
| 76 | M | >5x# | >5x# | Cholelithiasis | Discontinued | Recovered |
| 69 | M | >5x | >5x | Cholelithiasis | Continued | Recovered |
| 65 | M | >3x | — | Diarrhea | Continued | Recovered |
| 78 | M | — | >5x | Sepsis | Continued | 2 months after LFT increase, Patient died due to heart failure |
| 62 | M | — | >3x | [Isolated increase] | Continued | Recovered |
| 78 | M | >3x | — | [Isolated increase] | Continued | Recovered |
| 64 | F | >5x | >3x | [Isolated increase] | Discontinued | Recovered |

TABLE 2-continued

INDIVIDUAL PATIENTS WITH LFT ABNORMALITIES

| Age | Sex | ALT/ ULN | AST/ ULN | Alternative Diagnosis | Action taken with Study medicine | Final Outcome/ Comment |
|---|---|---|---|---|---|---|
| 81 | M | >5x | >3x | [Isolated increase] | [Off treatment] | Dabigatran was discontinued for a bleeding event 3 weeks prior to LFT increase |
| 74 | F | >3x# | >5x# | Gall stones | Reinstated | Recovered |
| 51 | M | — | >3x | Cholelithiasis | Continued | Recovered |
| 73 | M | >3x | — | Hepatitis | Continued | Recovered |
| 73 | F | >5x# | >5x# | Cholecystitis | Continued | Recovered |
| 68 | F | >3x | — | [Isolated increase] | Discontinued | Recovered |
| 68 | M | — | >5x | [Isolated increase] | Discontinued | Recovered |
| 63 | M | — | >5x | [Isolated increase] | Reinstated | Recovered | with concomitant Bilirubin elevation to >2xULN
ALT = Alanine Transaminase;
AST = Aspartate Transaminase;
Bili = Total Bilirubin;
F = Female;
M = Male;
ULN = Upper Limit of Normal Serious adverse events were recorded in 184 patients (51%), including bleeding and thrombotic events. The most common class of reported events was cardiac disorders (80 pts; 22%), followed by infections (34 pts; 9.4%), nervous system disorders (33 pts; 9.1%) and gastrointestinal disorders (28 pts; 7.8%). Other than bleeding and thrombotic events, no specific pattern emerged.

Major Bleeding Events

The incidence of bleeding events increased proportional to the dose. Major bleeding events are most frequent in patients taking 150 mg b.i.d. of dabigatran etexilate or more, with the highest rate reported in the 300 mg b.i.d. dabigatran etexilate group. Doses of 300 mg twice daily are not tolerable. The 150 mg b.i.d. dose has a rate of major bleeding slightly higher than that observed in recent anticoagulation trials in AF patients (Table 3). The five fatal bleeding events on dabigatran (0.5% per year) all occurred at either 150 mg b.i.d. (4 patients) or at 300 mg q.d. (1 patient). The intracranial bleed rate of 0.4% per year is within the range of 0.1% to 0.6% reported in other antithrombotic trials. There was also an increased risk of bleeding with concomitant ASA. In the RELY Clinical Trial, discussed in more detail below, aspirin doses of more than 100 mg a day are not allowed.

the same total dose given once daily, a possible explanation of the observed differences. The dose of 150 mg b.i.d. appears to strike the best balance between thromboembolic events and bleeding. Patients having at least one risk factor for major bleeding events as described and defined hereinbefore are

TABLE 3

Comparison between Recent AF trials and PETRO-Ex

|  | SPORTIF III (2003)[12] | SPORTIF V (2005)[13] | ACTIVE W (2006)[15] | BAFTA (2007)[20] | PETRO-Ex |
|---|---|---|---|---|---|
| Study Medicine or Interventions | Warfarin vs. Ximelagatran | Warfarin vs. Ximelagatran | Clopidogrel + ASA vs. Warfarin | ASA 75 mg/d vs. Warfarin | Dabigatran etexilate 150 mg b.i.d. vs 300 mg b.i.d. vs 300 mg q.d. vs 150 mg q.d. |
| N, participants | 3407 | 3922 | 6706 | 973 | 361 |
| Age (mean) | ~70 years | 71.6 years | 70.2 years | 81.4 years | 69.7 years |
| Male | 69% | 69% | 66% | 55% | 73% |
| Mean follow-up | 1.45 years | 1.66 years | 1.3 years | 2.7 years | 2.5 years |
| Myocardial Infarction | 1.1% (ximelagatran) 0.6% (warfarin) | 1.0% (ximelagatran) 1.4% (warfarin) | 0.6% (warfarin) | 1.1% (warfarin) | 0.7% (Dabigatran etexilate All doses) |
| LFT abnormalities >3xULN (per 100 patient years) | 6% (ximelagatran) 1% (warfarin) | 6% (ximelagatran) 0.8% (warfarin) | NR | NR | 1.7% (Dabigatran etexilate All doses) |
| Major bleeding events (per 100 patient years) | 1.3% (ximelagatran 36 mg b.i.d.) 1.7% (warfarin) | 2.4% (ximelagatran 36 mg b.i.d.) 3.1% (warfarin) | 2.2% (warfarin) | 1.9% (warfarin) | 3.2%* (Dabigatran etexilate 150 mg b.i.d.) |
| Stroke and systemic embolism (per 100 patient years) | 1.6% (ximelagatran 36 mg b.i.d.) 2.3% (warfarin) | 1.6% (ximelagatran 36 mg b.i.d.) 1.2% (warfarin) | 1.5% (warfarin) | 1.7% (warfarin) | 1.0% (Dabigatran etexilate 150 mg b.i.d.) |

*bleeding rate is without concomitant aspirin
ACTIVE W: Atrial Fibrillation Clopidogrel Trial With Irbesartan for Prevention of Vascular Events trial;
BAFTA = Birmingham Atrial Fibrillation Treatment of the Aged trial;
LFT = Liver Function Test;
PETRO Ex = Extension of Prevention of Embolic and Thrombotic Events in Patients With Persistent Atrial Fibrillation trial;
SPORTIF = Stroke Prevention using an oral direct Thrombin Inhibitor in atrial Fibrillation trial;
ULN = upper limit of normal Efficacy or Thromboembolic Events The limited data suggests that dabigatran etexilate has promising efficacy in stroke prevention. At the two highest doses, stroke or systemic thromboembolic event rates are approximately 1% per year, which is among the lowest reported rates in atrial fibrillation patients at moderate to high risk for stroke. This is similar to or better than the current standard oral standard therapy, warfarin. This dose is currently being studied on a larger scale in the phase 3 trial. Interestingly, the stroke rate on 300 mg once daily is higher than for 150 mg b.i.d., although this difference is not statistically significant.

Risk-Benefit

The data from this longitudinal, open-label study of several doses of dabigatran etexilate have established boundaries for both efficacy and safety. Doses of 150 mg per day or less appear to have unacceptably high rates of thromboembolic events with low bleeding rates, while doses of 600 mg per day produce unacceptable rates of bleeding though the stroke risk is low. The risk benefit for the 150 mg b.i.d. dose appears better than 300 mg q.d. with lower stroke rates but higher bleed rates. The pharmacokinetics of the divided dose yield a peak trough plasma concentration ratio of 2:1 versus 6:1 for preferably treated with a dosage of 110 mg b.i.d. dabigatran etexilate, possibly in the form of one of its pharmaceutically acceptable acid addition salts.

From the data presented in Table 1 and in FIG. 1 it can be obtained that twice daily (b.i.d.) application of dabigatran etexilate is preferable. Due to the rather low oral bioavailability of dabigatran etexilate on the one hand and the relatively high clearance of dabigatran on the other, the b.i.d. dosage scheme delivers more constant plasma levels of dabigatran.

As is demonstrated by a direct comparison of a 300 mg q.d. and 150 mg b.i.d. treatment regimen, the overall number of thromboembolic events is less under a b.i.d. regimen at the same daily dosage. Therefore the b.i.d. posology is preferred over the q.d. for comparable daily dosages. This also applies to the preferred b.i.d. dosage regimen for patients having at least one risk factor for major bleeding events of 100 mg to 120 mg b.i.d. Especially preferred is a b.i.d. dose of 110 mg dabigatran etexilate.

The data presented in Table 1 and FIG. 1 compare various dosages of dabigatran etexilate with respect to the occurrence of thromboembolic events and the risk of major bleeding events. The former is represented by the number of thromboembolic events per 100 years, the latter by the number of bleeding events per 100 years. "Years" or "Subject-years" is the sum (date of last drug intake–date of first drug intake+1) of all treated subjects/365.25.

When comparing the data the conclusion can be made that a dosage of 50 mg b.i.d. of dabigatran etexilate with more than 12 events per 100 years is not sufficient to achieve satisfactory thromboembolic relief.

Further, 300 mg b.i.d. of dabigatran etexilate, although resulting in a low number of thromboembolic events (about 1 event per 100 years), causes a rather high number of bleeding events (more than 12 per 100 years), which will render this dosage less suitable for a long term treatment scheme.

The data suggest two trends: In case of long term treatment, lowering the dosage from 300 mg b.i.d. to 150 mg b.i.d. the number of thromboembolic events remains constant at a low level. The number of bleeding events is significantly decreased when reducing the dosage from 300 mg b.i.d. to 150 mg b.i.d.

The treatment regimen of 150 mg of dabigatran etexilate b.i.d. provides better protection from thromboembolic events compared to 150 mg q.d. and 300 mg q.d. on the one hand and better protection from bleeding events than 300 mg b.i.d. while maintaining the same level of thromboembolic protection as 300 mg b.i.d. Considering a constant level of thromboembolic relief at dosages between 150 mg b.i.d. and 300 mg b.i.d., it has now been found that in patients having at least one risk factor for major bleeding events a further reduction of the dosage from 150 mg b.i.d. to a dosage range from 100 mg b.i.d. to 120 mg b.i.d. of dabigatran etexilate represents a very favorable balance between the number of thromboembolic events and the number of bleeding events. The daily dosage of 110 mg b.i.d. has proven to be a preferred balance between thromboembolic relief and drug safety in particular for patients having at least one risk factor for major bleeding events.

Thus, the above preferred dosage range of from 100 mg b.i.d. to 120 mg b.i.d., preferably 110 mg b.i.d., of dabigatran etexilate is considered to be suitable for treating atrial fibrillation in humans having at least one risk factor for major bleeding events for a period of time of 3 months, preferably 6 months, more preferably 9 months, more preferably 12 months, more preferably 24 months, more preferably 48 months, and more preferably 10 years or more.

Due to its prodrug nature, the treatment regimen according to this invention can be applied to other dabigatran ester or salt forms of Formula (III)

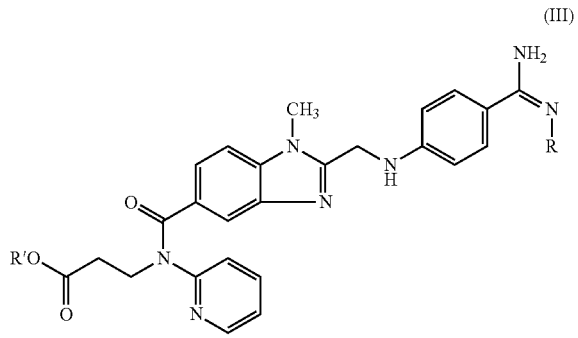

(III)

wherein R represents any ester moiety with molecular weight of up to 300, preferably of the formula —C(O)—O—$C_1$-$C_8$-alkyl or —C(O)—O—$C_3$-$C_8$-cycloalkyl, wherein the alkyl can optionally be branched or unbranched and the alkyl and the cycloalkyl can optionally be substituted and R' represents an —$C_1$-$C_8$-alkyl or —$C_3$-$C_8$-cycloalkyl, wherein the alkyl can optionally be branched or unbranched and the alkyl and the cycloalkyl can optionally be substituted.

Any formulation or modification of the compound of Formula (I) or (III) with a proven bioavailability of 80% to 125%, preferably of 80% to 120%, of the bioavailability obtainable by application of dabigatran etexilate according to this invention may also provide the same or comparable beneficial properties. Bioavailability is understood as the result of methods applied for demonstration of bioequivalence as recommended by the FDA or EMEA in the approval procedure of generic products referring to an already registered (approved) originator product.

The present invention also encompasses a dose unit comprising from 100 mg to 120 mg, preferably 110 mg of dabigatran etexilate for the treatment of atrial fibrillation. In a preferred embodiment the dose unit is a solid form, such as a tablet, capsule, granulate, powder, and the like. For example, such formulations are presented in the Formulations section below. In a particular preferred embodiment the solid form is a capsule containing dabigatran etexilate, coated on isolated tartaric acid core pellets. A particular preferred solid form is described in the Formulations section below.

More than 300 persons have finished both the PETRO and PETRO-Ex studies. These persons were representing different age and gender groups and had different weight and physical constitution. It has been found however that the results discussed above apply to all individuals likewise.

RELY Clinical Trial Results

The Randomized Evaluation of Long-term Anticoagulation Therapy (RELY) study was a randomized trial designed to compare two doses of dabigatran with warfarin in patients with atrial fibrillation who were at increased risk of stroke. The design of this study has been published in Ezekowitz M D, Connolly S J, Parekh A, Reilly P A, Varrone J, Wang S, Oldgren J, Themeles E, Wallentin L, and Yusuf S, *Rationale and design of the RE-LY: Randomized evaluation of long-term anticoagulant therapy, warfarin, compared to dabigatran*, Am Heart J., 2009, 157:805-810, which is herein incorporated by reference in its entirety.

In a non-inferiority trial, 18,113 patients with atrial fibrillation at risk of stroke were randomized to blinded fixed doses of dabigatran 110 mg or 150 mg twice daily versus unblinded adjusted warfarin. Median follow-up was 2.0 years and the primary outcome was stroke or systemic embolism. Rates of the primary outcome were 1.70% per year on warfarin versus 1.55% per year on dabigatran 110 mg (relative risk 0.91, 95% confidence interval 0.75 to 1.12; p [non-inferiority]<0.001) and 1.11% per year on dabigatran 150 mg (relative risk 0.66, 95% confidence interval 0.53 to 0.82; p [superiority]<0.001. Rates of major hemorrhage were 3.46% per year on warfarin versus 2.74% per year on dabigatran 110 mg (p=0.002) and 3.22% per year on dabigatran 150 mg (p=0.32). Rates of hemorrhagic stroke were 0.38% per year on warfarin versus 0.12% per year on dabigatran 110 mg (p<0.001) and 0.10% per year on dabigatran 150 mg (0.14-0.49; p<0.001). Mortality rates were 4.13% per year on warfarin versus 3.74% per year on dabigatran 110 mg (p<0.12) and 3.63% per year on dabigatran 150 mg (p<0.047).

Thus, in patients with atrial fibrillation, dabigatran 110 mg was associated with similar rates of stroke and systemic embolism to warfarin, but lower rates of major hemorrhage. Dabigatran 150 mg was associated with lower rates of stroke and systemic embolism than warfarin, but similar rates of major hemorrhage. Accordingly, dabigatran 110 mg demonstrated an improved safety profile over the warfarin therapy and dabigatran 150 mg demonstrated an improved efficacy over the warfarin therapy Details of the RELY Trial Methods Patients were recruited from 951 clinical centers in 44 countries. In brief, patients were eligible if they had atrial fibrillation documented on electrocardiogram at screening or within 6 months; and at least one of the following: prior stroke or transient ischemic attack; left ventricular ejection fraction less than 40%; New York Heart Association heart failure symptoms of Class 2 or greater within 6 months; age at least 75 years; or age at least 65 years with diabetes mellitus, hypertension or coronary artery disease. Reasons for exclusion included severe heart valve disorder; stroke within 14 days or severe stroke within 6 months; conditions which increased the risk of hemorrhage; creatinine clearance less than 30 mL/min; active liver disease; or pregnancy.

After providing written informed consent, all trial participants were randomly assigned to one of two doses of dabigatran or warfarin using a central interactive automated telephone system. Dabigatran was supplied in blinded capsules containing either 110 mg or 150 mg, taken twice daily. Warfarin was supplied in unblinded 1 mg, 3 mg, or 5 mg tablets and adjusted locally to an International Normalized Ratio (INR) of 2.0 to 3.0 with at least monthly INR measurements. The time in therapeutic range was calculated by the method of Rosendaal (Rosendaal F R, et al., A method to determine the optimal intensity of oral anticoagulant therapy, Thromb Haemost, 1993, 69:236-239), excluding INRs from the first week and after discontinuations. These data were reported back to centers with advice for optimal INR control. Concomitant use of aspirin (less than 100 mg/day) or other antiplatelet agents was allowed. Quinidine was prohibited 2 years after the trial started due to its potential to interact with dabigatran.

Patients were followed at 14 days after randomization, at 1 and 3 months, every 3 months thereafter in the first year and then every 4 months until study end. Liver function testing was performed monthly during the first year of follow-up. Following a pre-specified evaluation of liver function tests after 6000 dabigatran patients had been followed for 6 months or longer, the Data Monitoring Committee (DMC) recommended that liver function testing be reduced to occur at the regular visits.

The primary study outcome was stroke or systemic embolism. The primary safety outcome was major hemorrhage. Secondary outcomes were stroke, systemic embolism and death. Other outcomes were myocardial infarction, pulmonary embolism, transient ischemic attacks, and hospitalizations. The primary net benefit-risk outcome was the composite of stroke, systemic embolism, pulmonary embolism, myocardial infarction, death or major hemorrhage. Stroke was defined as sudden onset of focal neurological deficit consistent with the territory of a major cerebral artery and categorized as ischemic, hemorrhagic or unspecified. Hemorrhagic transformation of ischemic stroke was not considered as hemorrhagic stroke. Intracranial hemorrhage included hemorrhagic stroke and sub-dural or sub-arachnoid hemorrhage. Systemic embolism was an acute vascular occlusion of an extremity or organ documented by imaging, surgery or autopsy. Major bleeding was defined as a reduction in hemoglobin level of at least 2.0 g/L or transfusion of at least 2 units of blood or symptomatic bleeding in a critical area or organ. Life-threatening bleeding was a subset of major bleeding that included fatal bleeding, symptomatic intracranial bleeding, bleeding with hemoglobin decrease of more than 5.0 g/L or requiring transfusion of more than 4 units of blood or requiring inotropic agents or necessitating surgery. All other bleeding was considered minor.

All primary and secondary outcome events were blindly and doubly adjudicated. An international team of adjudicators reviewed documents in local languages after blinding; or documents were translated by a independent group and blinded centrally. All transient ischemic attacks were reviewed to ensure that strokes had not been missed. To detect possible unreported events, symptom questionnaires were regularly administered to patients, and adverse events and hospitalization reports were scrutinized for unreported primary or secondary outcomes.

Statistical Analysis

The primary analysis was designed to test if either dose of dabigatran was non-inferior to warfarin using Cox proportional hazard modeling. To satisfy the non-inferiority hypothesis, the upper bound of the one-sided 97.5% confidence interval of the relative risk (dabigatran:warfarin) needed to fall below 1.46. This non-inferiority margin was derived from a meta-analysis of trials of vitamin K antagonists against control in atrial fibrillation using the lower bound of that 95% confidence interval of the relative risk (warfarin: control). The margin of 1.46 would guarantee that 50% of the benefit of Vitamin K antagonists over control for reduction of stroke or systemic embolism would be preserved. To account for testing of both dabigatran doses against warfarin, we planned to test if the maximum of the two p-values was less than 0.025, one-sided, in which case both hypotheses would be rejected. If maximum of the two p-values was greater than 0.025, the minimum of the two p-values must be less than 0.0125, one-sided, to claim statistical significance. All analyses were based on intention-to-treat. We planned to enroll 15,000 patients, which we estimated would provide 84% power to evaluate non-inferiority of each dose of dabigatran. Two protocol changes were made by the Operations Committee during patient enrollment without knowledge of emerging treatment effects. These were enforcement of balanced enrollment of warfarin naïve (less than 61 days exposure to warfarin ever) and warfarin experienced patients; and an increase in study size to 18,000 patients to increase statistical power to compare each dabigatran dose against warfarin. An independent DMC reviewed unblinded study data and performed 2 pre-specified interim analyses of efficacy with a plan to recommend study termination if the benefit of dabigatran exceeded 3 standard deviations and persisted on repeat analysis 3 months later.

Patient Characteristics and Follow-Up

There were 18,113 patients enrolled between Dec. 22, 2005, and Dec. 15, 2007. Treatment groups were well balanced at baseline (Table 4). The mean age was 71 years and 64% were males. Half of patients were warfarin experienced. The mean CHADS2 score (a measure of stroke risk) was 2.1.

Final follow-up visits occurred between Dec. 15, 2008, and Mar. 15, 2009. The median follow-up was 2.0 years and was 99.9% complete, with 20 patients lost to follow-up. The rates of discontinuation for dabigatran 110 mg, dabigatran 150 mg, and warfarin were 14%, 15%, and 10% at one year and 23%, 25%, and 19% at 2.5 years, respectively. In-trial continuous aspirin use occurred in 23.5%, 21.6%, and 23.1% of patients on dabigatran 110 mg, dabigatran 150 mg, and warfarin, respectively. The mean time in therapeutic range for patients on warfarin was 64%.

TABLE 4

Baseline Characteristics

|  | Dabigatran 110 mg b.i.d. | Dabigatran 150 mg b.i.d. | Warfarin |
|---|---|---|---|
| Number randomized | 6015 | 6076 | 6022 |
| Mean age (yrs) (SD) | 71.4 (8.6) | 71.5 (8.8) | 71.6 (8.6) |
| Mean weight (kg) (SD) | 82.9 (19.9) | 82.46 (19.4) | 82.70 (19.7) |
| Mean BP systolic (mmHg) (SD) | 130.8 (17.5) | 131.0 (17.6) | 131.2 (17.4) |
| Mean BP diastolic (mmHg) (SD) | 77.0 (10.6) | 77.0 (10.6) | 77.1 (10.4) |
| Male (%) | 3865 (64.3) | 3840 (63.2) | 3809 (63.3) |
| AF type |  |  |  |
| Persistent (%) | 1950 (32.4) | 1909 (31.4) | 1930 (32.0) |
| Paroxysmal (%) | 1929 (32.1) | 1978 (32.6) | 2036 (33.8) |
| Permanent (%) | 2132 (35.4) | 2188 (36.0) | 2055 (34.1) |
| CHADS$_2$ Score** (mean) (SD) | 2.1 (1.1) | 2.2 (1.2) | 2.1 (1.1) |
| 0-1 (%) | 1958 (32.6) | 1958 (32.2) | 1862 (30.9) |
| 2 (%) | 2088 (34.7) | 2137 (35.2) | 2230 (37.0) |
| 3-6 (%) | 1968 (32.7) | 1981 (32.6) | 1933 (32.1) |
| Prior stroke or Transient Ischemic Attack (%) | 1195 (19.9) | 1233 (20.3) | 1195 (19.8) |
| Prior Myocardial infarction (%) | 1008 (16.8) | 1029 (16.9) | 968 (16.1) |
| Heart failure (%) | 1937 (32.2) | 1934 (31.8) | 1922 (31.9) |
| Diabetes Mellitus (%) | 1409 (23.4) | 1402 (23.1) | 1410 (23.4) |
| Hypertension (%) | 4738 (78.8) | 4795 (78.9) | 4750 (78.9) |
| Baseline Medications |  |  |  |
| Aspirin | 2404 (40.0) | 2352 (38.7) | 2442 (40.6) |
| ARB or ACE I | 3987 (66.3) | 4053 (66.7) | 3939 (65.5) |
| Beta-blocker | 3784 (62.9) | 3872 (63.7) | 3719 (61.8) |
| Amiodarone | 624 (10.4) | 665 (10.9) | 644 (10.7) |
| Statin | 2698 (44.9) | 2667 (43.9) | 2673 (44.4) |
| Proton pump inhibitor | 812 (13.5) | 847 (13.9) | 832 (13.8) |
| H$_2$ receptor antagonist | 225 (3.7) | 241 (4.0) | 256 (4.3) |
| Warfarin inexperienced* | 3011 (50.1) | 3049 (50.2) | 2929 (48.6) |

Figure 2:
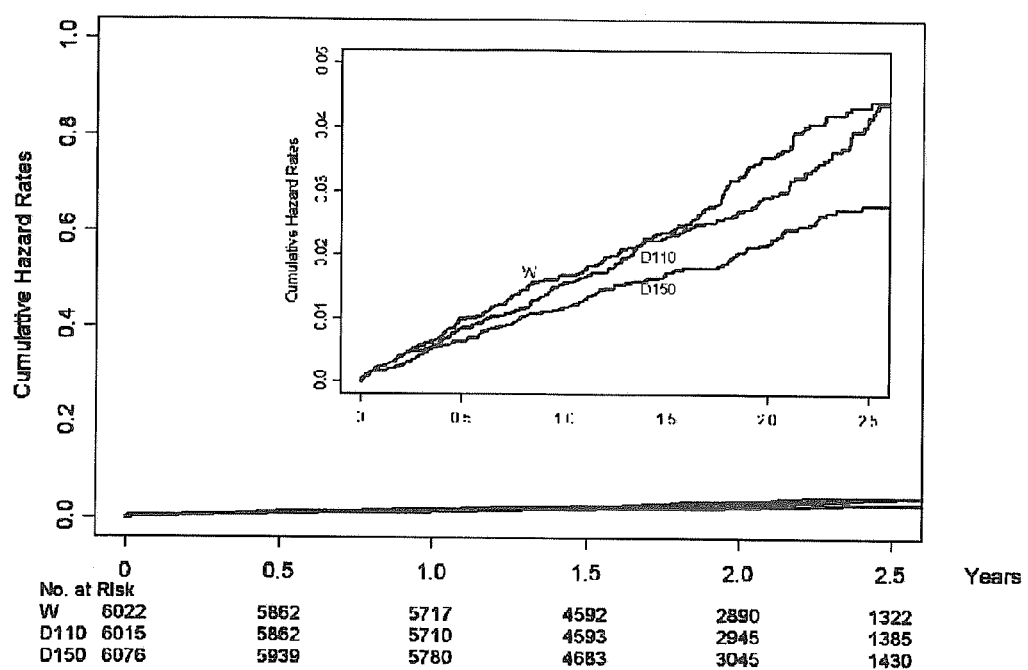
FIG. 2: Cumulative Risk of Stroke or Systemic Embolism for Dabigatran 110 mg and 150 mg twice daily and for warfarin (W=warfarin; D110=dabigatran 110 mg b.i.d.; D150=dabigatran 150 mg b.i.d.

*By study definition of <2 months of vitamin K antagonist use ever.
**CHADS2 score = a common stroke risk stratification score which gives one point each for congestive heart failure, hypertension, age ≥75, diabetes mellitus, and 2 points for prior stroke or TIA (16)
Abbreviations:
AF = atrial fibrillation,
ARB = angiotensin receptor blocker,
ACE-I = angiotensin converting enzyme inhibitor,
statin = HMG-CoA reductase inhibitors Primary Outcome Stroke or systemic embolism occurred in 182 patients on dabigatran 110 mg (1.55% per year), 133 patients on dabigatran 150 mg (1.11% per year) and in 198 patients on warfarin (1.70% per year) (Table 5 and FIG. 2). Both doses of dabigatran were non-inferior to warfarin (p<0.001). Dabigatran 150 mg was also superior to warfarin (relative risk [RR] 0.66, 95% confidence interval [CI] 0.53 to 0.82; p<0.001), but dabigatran 110 mg was not (RR 0.91, 95% CI 0.75 to 1.12; p=0.37). Rates of hemorrhagic stroke were 0.38% per year on warfarin compared with 0.12% per year on dabigatran 110 mg (RR 0.31 95% CI 0.17 to 0.56; p<0.001) and 0.10% per year on dabigatran 150 mg (RR 0.26, 95% CI 0.14 to 0.49; p<0.001).

TABLE 5

Efficacy Outcomes

| Event | Dabigatran 110 mg N = 6015 | | Dabigatran 150 mg N = 6076 | | Warfarin N = 6022 | | Dabigatran 110 mg vs. Warfarin | | | Dabigatran 150 mg vs. Warfarin | | | Dabigatran 150 mg vs. 110 mg | | |
|---|---|---|---|---|---|---|---|---|---|---|---|---|---|---|---|
|  | N | Rate | N | Rate | N | Rate | RR | CI | P | RR | CI | P | RR | CI | P |
| Stroke or systemic embolism | 182 | 1.55 | 133 | 1.11 | 198 | 1.70 | 0.91 | 0.75-1.12 | <0.001 (NI) 0.37 (sup) | 0.66 | 0.53-0.82 | <0.001 (NI) <0.001 (sup) | 0.72 | 0.58-0.90 | 0.004 |
| Stroke | 171 | 1.45 | 121 | 1.01 | 184 | 1.58 | 0.92 | 0.75-1.14 | 0.44 (sup) | 0.64 | 0.51-0.81 | <0.001 (sup) | 0.70 | 0.55-0.88 | 0.002 |
| Hemorrhagic | 14 | 0.12 | 12 | 0.10 | 45 | 0.38 | 0.31 | 0.17-0.56 | <0.001 (sup) | 0.26 | 0.14-0.49 | <0.001 (sup) | 0.85 | 0.39-1.83 | 0.67 |
| Ischemic or Unspecified | 159 | 1.35 | 110 | 0.92 | 141 | 1.21 | 1.12 | 0.89-1.41 | 0.32 (sup) | 0.76 | 0.59-0.98 | 0.034 (sup) | 0.68 | 0.53-0.87 | 0.002 |
| Non-disabling Stroke Modified Rankin 0-2 | 60 | 0.51 | 43 | 0.36 | 68 | 0.58 | 0.87 | 0.62-1.24 | 0.45 (sup) | 0.62 | 0.42-0.91 | 0.01 (sup) | 0.71 | 0.48-1.05 | 0.08 |
| Disabling or Fatal Stroke Modified Rankin 3-6 | 112 | 0.95 | 80 | 0.67 | 118 | 1.01 | 0.94 | 0.73-1.22 | 0.65 (sup) | 0.66 | 0.50-0.88 | 0.005 (sup) | 0.70 | 0.53-0.94 | 0.02 |
| Myocardial Infarction | 86 | 0.73 | 89 | 0.74 | 63 | 0.54 | 1.35 | 0.98-1.87 | 0.069 (sup) | 1.38 | 1.00-1.91 | 0.048 (sup) | 1.02 | 0.76-1.38 | 0.89 |
| Pulmonary embolism | 14 | 0.12 | 18 | 0.15 | 11 | 0.09 | 1.26 | 0.57-2.78 | 0.56 (sup) | 1.61 | 0.76-3.42 | 0.21 (sup) | 1.27 | 0.63-2.56 | 0.50 |
| First Hospitalization | 2311 | 25.1 | 2430 | 26.7 | 2458 | 27.5 | 0.92 | 0.87-0.97 | 0.003 (sup) | 0.97 | 0.92-1.03 | 0.34 (sup) | 1.06 | 1.00-1.12 | 0.04 |
| Vascular Death | 288 | 2.42 | 273 | 2.27 | 317 | 2.69 | 0.90 | 0.77-1.06 | 0.19 (sup) | 0.84 | 0.72-0.99 | 0.038 (sup) | 0.94 | 0.79-1.11 | 0.44 |
| All Death | 445 | 3.74 | 437 | 3.63 | 487 | 4.13 | 0.90 | 0.79-1.03 | 0.12 (sup) | 0.88 | 0.77-1.00 | 0.047 (sup) | 0.97 | 0.85-1.11 | 0.66 |

NI = non-inferiority,
sup = superiority
Rate = Rate/100 Person Years
CI = 95% Confidence Interval Other Outcomes Rates of death from any cause were 4.13% per year on warfarin compared with 3.74% per year on dabigatran 110 mg (RR 0.90, 95% CI 0.79 to 1.03; p=0.12), and 3.63% per year on dabigatran 150 mg (RR 0.88, 95% CI 0.77 to 1.00; p=0.047). Myocardial infarction occurred at a rate of 0.54% per year on warfarin and more often on dabigatran; at 0.73% per year on 110 mg (RR 1.35, 95% CI 0.98 to 1.87; p=0.069), and at 0.74% per year on 150 mg (RR 1.38, 95% CI 1.00 to 1.91; p=0.048).

Bleeding

Rates of major bleeding were 3.46% per year on warfarin compared with 2.74% per year on dabigatran 110 mg (RR 0.79, 95% CI 0.68 to 0.92; p=0.002) and 3.22% per year on dabigatran 150 mg (RR 0.93, 95% CI 0.81 to 1.07; p=0.32) (Table 6). Rates of life-threatening bleeding, intracranial bleeding, and total bleeding were higher with warfarin than with either dose of dabigatran. With dabigatran 150 mg, there was a higher rate of major gastrointestinal bleeding than with warfarin.

All p values are for superiority. Hemorrhagic stroke was counted both as a stroke in Table 5, as a major/life-threatening bleeding and is part of intracranial bleeding in Table 6.

The net benefit-risk outcome consisted of major vascular events, major bleeding and death. The rates of this combined end point were 7.99% per year on warfarin compared with 7.37% per year on dabigatran 110 mg (RR 0.92, 95% CI 0.84 to 1.01; p=0.097) and 7.22% per year on dabigatran 150 mg (RR 0.90, 95% CI 0.82 to 0.99; p=0.04).

Comparison of Dabigatran Doses

Compared to the 110 mg dose, dabigatran 150 mg reduced the risk of stroke or systemic embolism (p=0.004). This difference was driven mostly by a decrease in stroke of ischemic or unspecified etiology, while rates of hemorrhagic stroke were similar in both groups. There was no difference in either vascular or total mortality between the doses. On the other hand, as compared to dabigatran 110 mg, 150 mg increased the risk of major bleeding (p=0.04) and also increased gastrointestinal, minor, and total bleeding. The net clinical benefit was almost identical for the two doses.

Adverse Events and Liver Function Testing

There was an increase in adverse events related to dyspepsia with dabigatran (Table 7). Serum aspartate or alanine aminotransferase elevations of greater than 3 times the upper limit of normal did not occur more frequently with dabigatran at either dose than with warfarin.

TABLE 7

Study Drug Discontinuation, Adverse Events and Liver Function Tests

| | Dabigatran 110 mg (%) N = 6015 | Dabigatran 150 mg (%) N = 6076 | Warfarin (%) N = 6022 |
|---|---|---|---|
| Study Drug Discontinuation | | | |
| At one year | XXXX (14) | XXXX (15) | XXXX (10) |
| At two years | XXXX (23) | XXXX (25) | XXXX (19) |

TABLE 6

Bleeding and Net Benefit

| | Dabigatran 110 mg | | Dabigatran 150 mg | | Warfarin | | Dabigatran 110 mg vs. Warfarin | | | Dabigatran 150 mg vs. Warfarin | | | Dabigatran 150 mg vs. 110 mg | | |
|---|---|---|---|---|---|---|---|---|---|---|---|---|---|---|---|
| Event | N | Rate | N | Rate | N | Rate | RR | CI | P | RR | CI | P | RR | CI | P |
| Any Major Bleeding | 318 | 2.74 | 375 | 3.22 | 396 | 3.46 | 0.79 | 0.68-0.92 | 0.002 | 0.93 | 0.81-1.07 | 0.32 | 1.17 | 1.01-1.36 | 0.04 |
| Life threatening | 143 | 1.21 | 175 | 1.47 | 210 | 1.80 | 0.67 | 0.54-0.83 | <0.001 | 0.82 | 0.67-1.00 | 0.047 | 1.21 | 0.97-1.51 | 0.09 |
| Other Major | 196 | 1.67 | 226 | 1.92 | 208 | 1.80 | 0.93 | 0.77-1.14 | 0.50 | 1.07 | 0.89-1.29 | 0.48 | 1.14 | 0.95-1.39 | 0.17 |
| Minor Bleeding | 1566 | 16.22 | 1787 | 18.87 | 1930 | 21.03 | 0.79 | 0.74-0.84 | <0.001 | 0.91 | 0.86-0.97 | 0.005 | 1.16 | 1.08-1.24 | <0.001 |
| Major or Minor Bleeding | 1740 | 18.38 | 1977 | 21.39 | 2141 | 23.92 | 0.78 | 0.74-0.84 | <0.001 | 0.91 | 0.86-0.97 | 0.002 | 1.16 | 1.09-1.23 | <0.001 |
| Intracranial Bleeding | 25 | 0.21 | 36 | 0.30 | 85 | 0.72 | 0.29 | 0.19-0.45 | <0.001 | 0.41 | 0.28-0.61 | <0.001 | 1.42 | 0.86-2.37 | 0.17 |
| Extracranial Bleeding | 295 | 2.24 | 342 | 2.93 | 314 | 2.73 | 0.93 | 0.79-1.09 | 0.38 | 1.07 | 0.92-1.25 | 0.36 | 1.15 | 0.99-1.35 | 0.08 |
| Major gastro-intestinal Bleeding | 133 | 1.13 | 182 | 1.54 | 120 | 1.03 | 1.10 | 0.86-1.41 | 0.43 | 1.50 | 1.19-1.89 | <0.001 | 1.36 | 1.09-1.70 | 0.007 |
| Stroke, systemic embolism, pulmonary embolism, myocardial infarction death or major bleed | 842 | 7.37 | 830 | 7.22 | 900 | 7.99 | 0.92 | 0.84-1.01 | 0.097 | 0.90 | 0.82-0.99 | 0.04 | 0.98 | 0.89-1.08 | 0.66 |

Rate: Rate/100 Person Years
CI: 95% Confidence Interval

TABLE 7-continued

Study Drug Discontinuation, Adverse Events and Liver Function Tests

| | Dabigatran 110 mg (%) N = 6015 | Dabigatran 150 mg (%) N = 6076 | Warfarin (%) N = 6022 |
|---|---|---|---|
| Reason for discontinuation: | | | |
| Patient decision | XXX (7.3) | XXX (7.8) | XXX (6.2) |
| Outcome event | XXX (3.2) | XXX (2.7) | XXX (2.2) |
| SAE** | 156 (2.6) | 158 (2.6) | 95 (1.6) |
| Gastrointestinal disorders† | XXX (2.7) | XXX (2.8) | XXX (0.8) |
| Gastrointestinal bleeding | XXX (1.0) | XXX (1.4) | XXX (0.9) |

TABLE 7-continued

Study Drug Discontinuation, Adverse Events and Liver Function Tests

|  | Dabigatran 110 mg (%) N = 6015 | Dabigatran 150 mg (%) N = 6076 | Warfarin (%) N = 6022 |
|---|---|---|---|
| Adverse Event* | | | |
| Dyspepsia** | 367 (6.1) | 345 (5.7) | 83 (1.4) |
| Dizziness | 457 (7.6) | 458 (7.6) | 555 (9.3) |
| Dyspnoea | 497 (8.3) | 525 (8.7) | 550 (9.2) |
| Peripheral edema | 446 (7.5) | 442 (7.3) | 453 (7.6) |
| Fatigue | 370 (6.2) | 367 (6.1) | 353 (5.9) |
| Cough | 319 (5.3) | 310 (5.1) | 345 (5.8) |
| Chest pain | 288 (4.8) | 355 (5.9) | 342 (5.7) |
| Back pain | 295 (4.9) | 289 (4.8) | 331 (5.5) |
| Arthralgia | 249 (4.2) | 313 (5.2) | 328 (5.5) |
| Nasopharyngitis | 314 (5.2) | 309 (5.1) | 327 (5.5) |
| Diarrhea | 355 (5.9) | 367 (6.1) | 327 (5.5) |
| Atrial fibrillation | 303 (5.1) | 313 (5.2) | 326 (5.4) |
| Urinary tract infection | 242 (4.0) | 253 (4.2) | 315 (5.3) |
| Upper respiratory tract infection | 266 (4.4) | 261 (4.3) | 297 (5.0) |
| Liver Function Test Abnormalities | | | |
| ALT or AST >3xULN | 121 (2.0) | 111 (1.8) | 126 (2.1) |
| ALT or AST >3xULN with concurrent bilirubin >2xULN | 11 (0.2) | 14 (0.2) | 22 (0.4) |
| Hepatobiliary Adverse Events | | | |
| hepatobiliary disorders (SAE)¶ | 25 (0.4) | 28 (0.5) | 25 (0.4) |
| hepatobiliary disorders (AE)£ | 121 (2.0) | 123 (2.0) | 132 (2.2) |

†Including pain, vomiting and diarrhea.
*Includes adverse events reported in >5% of the overall population. Based on reports occurring on study treatment.
**Occurred less frequently on warfarin than on either dose of dabigatran (p < 0.001).
ALT = alanine aminotransferase,
AST = aspartate aminotransferase,
AE = adverse event,
SAE = serious adverse event,
ULN = upper limit of normal.
¶Clinical and/or biochemical liver dysfunction requiring hospitalization.
£Jaundice, nausea and vomiting, abdominal pain, itching, lethargy and fatigue Important Sub-Groups For most of the pre-specified subgroups, no significant interaction with the treatment effect of dabigatran (at either dose) was seen (FIG. 3). There was no significant interaction between the treatment effect of dabigatran and prior warfarin experience. Although dabigatran is 80% renally excreted, there was no interaction with baseline calculated creatinine clearance.

Discussion

In the RELY trial, two blinded fixed-dose regimens of dabigatran (110 mg twice daily and 150 mg twice daily) were compared with adjusted-dose warfarin in patients with atrial fibrillation at risk of stroke. Both dabigatran doses were non-inferior to warfarin with respect to the primary efficacy end point of stroke or systemic embolism. In addition, the higher dose was superior with respect to stroke or systemic embolism and the lower dose was superior with respect to major bleeding. Furthermore, the higher dose of dabigatran was associated with fewer total deaths and deaths from vascular cause than warfarin.

Previous studies seeking to identify a safe and effective alternative to warfarin in patients with atrial fibrillation have all suffered from specific limitations. The combination of clopidogrel and aspirin was more effective than aspirin alone, The ACTIVE Investigators, Effect of Clopidogrel Added to Aspirin in Patients with Atrial Fibrillation, N Engl J Med. 2009, 360, but less effective than warfarin, ACTIVE Writing Group of the ACTIVE Investigators, Clopidogrel plus aspirin versus oral anticoagulation for atrial fibrillation in the Atrial Fibrillation Clopidogrel Trial with Irbesartan for Prevention of Vascular Events (ACTIVE W): a randomized controlled trial, Lancet, 2005, 367:1903-1912. Sub-cutaneous idraparinux was more effective than warfarin but with a substantially higher risk of bleeding, Amadeus Investigators, et al., Comparison of idraparinux with vitamin K antagonists for prevention of thromboembolism in patients with atrial fibrillation: a randomized, open-label, non-inferiority trial, Lancet, 2008 Jan. 26, 371 (9609):315-321. Ximelagatran, an earlier direct thrombin inhibitor, appeared to have similar efficacy and safety to warfarin, but was found to be hepatotoxic, Deiner H C, Executive Steering Committee Stroke Prevention Using the Oral Direct Thrombin Inhibitor Ximelagatran in Patients with Non-Valvular Atrial Fibrillation Pooled Analysis from the SPORTIF III and V Studies, Cerebrovasc Dis, 2006, 21:279-293. In contrast, in the serial measurement of liver function tests, there was no evidence of hepatotoxicity with dabigatran.

The most devastating complication of warfarin therapy is intracranial hemorrhage, especially hemorrhagic stroke. Compared to aspirin, warfarin doubles the risk of intracranial hemorrhage, Hart, R G, supra. It is therefore an important advantage of both doses of dabigatran that they reduced this complication compared to warfarin by more than two thirds, without compromising efficacy against ischemic stroke. The rate of major bleeding on warfarin was higher in this study than in some previous trials (Deiner H C, supra; The ACTIVE Investigators, supra; ACTIVE Writing Group of the ACTIVE Investigators, supra). This is partly explained by a more inclusive definition of major bleeding in this study. There was an increase in gastrointestinal bleeding with the higher dabigatran dose despite the overall lower rates of bleeding at other sites. To enhance absorption of dabigatran, a low pH is required. Therefore, dabigatran capsules contain dabigatran-coated pellets with a tartaric acid core. This acidity may explain the increased incidence of dyspeptic symptoms with both dabigatran doses and the increased risk of gastrointestinal bleeding with the 150 mg dose.

The benefit of dabigatran may be explained in part by the twice daily dosing of dabigatran, which, with an elimination half-life of 12 to 17 hours, reduces variability in anticoagulant effect, especially compared to warfarin, which is difficult to control. Warfarin broadly inhibits coagulation (inhibiting Factors II, VII, IX, X, Proteins C and S). By selectively inhibiting only thrombin, dabigatran may achieve antithrombotic efficacy while preserving some other hemostatic mechanisms in the coagulation system to mitigate potential bleeding.

Limitations of the study are its use of open-label warfarin, which could have introduced a potential bias in reporting or adjudication of events; and its relatively short duration of follow-up. The decision not to blind adjusted dose warfarin was based on the goal to have the most realistic dosing of warfarin and on the expectation that warfarin un-blinding would often occur at the time of events. Control of warfarin anticoagulation was comparable to that in previously reported global clinical trials (with a time in therapeutic range of 64%), even though half of our patients were warfarin naïve, a group less likely to have good control (Rosendaal F R, et al., supra; The ACTIVE Investigators, supra).

The net outcome in terms of overall benefit and risk was comparable between the two doses of dabigatran. However, this overall similarity is due to that fact that the lower ischemic risk with dabigatran 150 mg is balanced by the lower hemorrhagic risk with dabigatran 110 mg. These findings suggest that the dose of dabigatran could potentially be tailored to specific patient risk characteristics, although this concept was not specifically tested in our trial. The results of the clinical investigations suggest that the use of 110 mg b.i.d. dabigatran etexilate, possibly in form of its pharmaceutically acceptable acid addition salts, is particularly preferred in patients having at least one risk factor for major bleeding events.

In conclusion, we compared two doses of dabigatran with warfarin in patients with atrial fibrillation at risk of stroke. Dabigatran 110 mg was associated with similar rates of stroke and systemic embolism, and lower rates of major hemorrhage, than warfarin. Dabigatran 150 mg was associated with lower rates of stroke and systemic embolism, and similar rates of major hemorrhage.

Contraindications and Special Warnings and Precautions

There are several contraindications for treatment with dabigatran: known hypersensitivity to dabigatran or dabigatran etexilate or to one of the excipients of the product; patients with severe renal impairment (creatine clearance of <30 mL/min); hemorrhagic manifestations, active bleeding, patients with a bleeding diathesis, or patients with spontaneous or pharmacological impairment of hemostasis; organ lesions at risk of clinically significant bleeding, including hemorrhagic stroke within the last 6 months; patients with an indwelling spinal or epidural catheter and during the first hour after removal; and concomitant treatment with quinidine, verpamil, etc. or alternatively concom P-gp inhibitors.

Hepatic Impairment: Patients with moderate and severe hepatic impairment (Child-Pugh classification B and C) or liver disease expected to have any impact on survival including but not limited to the persistent elevation of liver enzymes >2 Upper Limit Normal (ULN), or hepatitis A, B, or C, or expected to have any impact on survival were excluded in clinical trials. Therefore the use of dabigatran etexilate is generally not recommended in this population.

Hemorrhagic Risk: Due to the pharmacological mode of action, the use of dabigatran etexilate can principally lead to an increased risk of bleeding complications. In addition, factors, such as renal function or strong P-gp-inhibitor comedication are known to increase dabigatran plasma levels to different degrees. As has been shown in different clinical settings, an increase in dabigatran plasma levels does not automatically lead to an increased bleeding risk. In those cases, where such factors are known to increase the bleeding risk and outweigh the clinical benefit, posology recommendations are given as appropriate. If different multivariate factors may lead to an unknown hemorrhagic risk it is advised to carefully monitor patients for signs of bleeding complications.

The instant invention is also preffrably directed to a method for the treatment of patients that are characterized by an increased risk of major bleeding events (i.e., at least one risk factor for major bleeds), the method comprising monitoring patients for signs of bleeding events, particularly major bleeding events, and administration of dabigatran etexilate, optionally in the form of one of its pharmaceutically acceptable acid addition salts, in an amount of 110 mg b.i.d.

Close observation (looking for signs of bleeding or anemia) is generally required in the following situations that may increase the hemorrhagic risk: (a) recent biopsy, major trauma, or shortly after brain, spinal, or ophthalmologic surgery; (b) treatments liable to increase the hemorrhagic risk, as the association of dabigatran etexilate with treatments that act on hemostasis or coagulation may increase the hemorrhagic risk; and (c) bacterial endocarditis, congenital or acquired bleeding disorders, active ulcerative and angiodysplastic gastrointestinal disease, and hemorrhagic stroke (6 months).

In addition, an increase in the risk of bleeding can occur via specific pharmacokinetic or pharmacodynamic interactions with some concomitant medications and the following treatments should generally not be administered concomitantly with dabigatran etexilate: unfractionated heparins and heparin derivatives, low molecular weight heparins (LMWH), fondaparinux, desirudin, thrombolytic agents, GPIIb/IIIa receptor antagonists, dextran, sulfinpyrazone, rivaroxaban, prasugrel, and vitamin K antagonists. It should be noted that unfractionated heparin can be administered at doses necessary to maintain a patent central venous or arterial catheter. The oral application of the strong P-gp inhibitors verapamil, quinidine or amiodarone concomitantly with dabigatran etexilate is known to elevate dabigatran plasma concentrations which may also result in an increased bleeding risk.

Formulations

Dabigatran etexilate is preferably formulated as the methanesulfonate salt (WO 03/074056). The following examples are for illustrating dosage forms according to the present invention and methods for the production thereof that have been applied in the clinical trials referred to in this patent application.

The process for the manufacture of the pharmaceutical compositions used in the mentioned clinical trials is characterized by a series of partial steps. First, the core 1 is produced from pharmaceutically acceptable organic acid. Within the scope of the present invention tartaric acid is used to prepare the core 1. The core material 1 thus obtained is then converted into so-called isolated tartaric acid cores 3 by spraying on an isolating suspension 2. A dabigatran suspension 4 prepared subsequently is sprayed onto these coated cores 3 in one or more process steps by means of a coating process. Finally, the active substance pellets 5 thus obtained are packed into suitable capsules.

Determining the Particle Sizes of Tartaric Acid by Air Jet Screening

Measuring Device and Settings

Measuring Device: Air jet screen, e.g., Alpine A 200 LS

Screens: As required

Weight Put In: 10 g/screen

Duration: 1 min/screen, then 1 min each up to the maximum weight loss of 0.1 g

Preparation of Sample/Supply of Product

The substance is transferred into a mortar and any lumps present are destroyed by intensive pounding. The screen with rubber seal and cover is placed on a balance, set to zero, and 10.0 g of the pounded substance are weighed onto the screen. The screen together with its contents, rubber seal, and cover are placed on the device. The timer is set to 1 minute and the material is treated by air jet screening for this time. Then the residue is weighed out and documented. This process is repeated until the decrease in the weight of the residue after air jet screening is <0.1 g.

Example 1

Preparation of the Starter Pellets 480 kg of water is heated to 50° C. and 120 kg of acacia (gum arabic) are added with stirring in a conventional mixing container having a dished end and stirrer. Stirring is continued at constant temperature until a clear solution is obtained. Once there is a clear solution (usually after 1 to 2 hours), 600 kg of tartaric acid are added with stirring. The tartaric acid is added at constant temperature while stirring is continued. After the addition has ended, the mixture is stirred for about another 5 to 6 hours.

1000 kg of tartaric acid is added to a slowly rotating (3 revolutions per minute) unperforated horizontal pan with a spraying and powder applying unit (e.g., Driamat 2000/2.5). Before spraying starts, a sample of the acid is taken for screening analysis. The acid in question is tartaric acid particles with a particle size in the range from 0.4-0.6 mm. The acid rubber solution obtained by the above method is sprayed onto the tartaric acid particles thus provided. During the spraying, the quantity of air supplied is adjusted to 1000 m$^3$/h and 35° C.-75° C. The differential pressure is 2 mbar and the speed of rotation of the pan is 9 revolutions per minute. The nozzles should be arranged at a distance of 350-450 mm from the filling.

The acid rubber solution is sprayed on by alternating with the following steps. After about 4.8 kg of the acid rubber solution has been sprayed onto the tartaric acid particles of particle size 0.4-0.6 mm and the solution has been distributed, about 3.2 kg of tartaric acid powder is sprinkled onto the damp tartaric acid particles. The tartaric acid powder in question consists of fine tartaric acid particles with a particle size of <50 microns. In all, 800 kg of tartaric acid powder are required. After the tartaric acid powder has been sprinkled on and distributed the spray material is dried until a product temperature of about 40° C. is reached. This is in turn followed by the spraying on of the acid rubber solution.

These cycles are repeated until the acid rubber solution is used up. Once the process has ended, the acid pellets are dried in the pan at 3 rpm for 240 minutes. To prevent caking after the drying has finished, an intermittent program is run at 3 rpm for 3 minutes every hour. In the present instance, this means that the pan is rotated at 3 rpm for 3 minutes at intervals of one hour and then left to stand. The acid pellets are then transferred into a dryer. They are then dried at 60° C. over a period of 48 hours. Finally, the particle size distribution is determined by screen analysis. The particle size with a diameter of 0.6-0.8 mm corresponds to the product. This fraction should make up >85%.

Example 2

Isolation of the Starter Pellets

To prepare the isolating suspension, 666.1 kg of ethanol are placed in the mixing container and the hydroxypropylmethylcellulose (33.1 kg) is added with stirring at approx. 600 rpm and dissolved. Then under the same conditions 0.6 kg dimethicone are added. Shortly before use, talc (33.1 kg) is added, again with stirring, and suspended.

The acid pellets 1200 kg are poured into the coating apparatus (e.g. GS-Coater Mod. 600/Mod. 1200) and sprayed therein in the rotating pan with the isolating suspension described above in a continuous spraying process lasting several hours at a spraying rate of 32 kg/h for the 1200 kg mixture or 21 kg/h for the 600 kg mixture. The pellets are also dried continuously with an air supply at up to 70° C.

After the GS-Coater has been emptied, the isolated starter pellets are fractionated by screening. The product fraction with a diameter ≤1.0 mm is stored and used further.

Example 3

Preparation of the Dabigatran Etexilate Suspension 26.5 kg of hydroxypropylcellulose are added to 720 kg of isopropanol in a 1200 L mixing container fitted with a propeller stirrer and the mixture is stirred until fully dissolved (about 12 to 60 hours; roughly 500 rpm). Once the solution is clear, 132.3 kg of dabigatran etexilate methanesulfonate (polymorph I) is added with stirring (400 rpm) and the mixture is stirred for about another 20 to 30 minutes. Then 21.15 kg of talc is added at a constant stirring rate and stirring is continued at the same speed for about another 10 to 15 minutes. The steps described above are preferably carried out under a nitrogen atmosphere.

Any clumps formed are broken up by homogenizing using an UltraTurrax stirrer for about 60 to 200 minutes. The suspension temperature should not exceed 30° C. throughout the entire manufacturing process.

The suspension is stirred until ready for further processing to ensure that no sedimentation occurs (at roughly 400 rpm).

If the suspension is stored at below 30° C., it should be further processed within at most 48 hours. If, for example, the suspension is manufactured and stored at 22° C., it may be further processed within 60 hours. If the suspension is stored, for example, at 35° C., it should be further processed within at most 24 hours.

Example 4

Preparation of the Dabigatran Etexilate Active Substance Pellets

A horizontal pan with an unperforated container is used (GS Coater Mod. 600). In contrast to the fluidized bed method, the suspension is sprayed onto the fluidized bed of pellets in the rotating pan by the "top spray" method. It is sprayed on through nozzles 1.4 mm in diameter. The dry air is passed into the bed of pellets through so-called immersion blades and transported away through an opening in the back wall of the coater.

The horizontal pan is charged with 320 kg of the tartaric acid pellets obtained according to Example 2 and the bed of pellets is heated up. Once a product temperature of 43° C. has been reached, spraying begins. 900 kg of the suspension prepared previously according to Example 3 is sprayed on, first for 2 hours at a spraying rate of 20 kg/h, then at 24 kg/h and a spray pressure of 0.8 bar. The suspension is stirred constantly. The temperature of the air supplied is at most 75° C. The amount of air supplied is about 1900 m$^3$/h.

Then the pellets are dried in the horizontal pan (5 revolutions per minute) at an air inflow temperature of at least 30° C., at most 50° C., and an air inflow amount of 500 m$^3$/h over a period of about 1 to 2 hours.

325 kg of the pellets thus obtained are then loaded once more into a horizontal pan and heated to 43° C. 900 kg of the suspension prepared previously according to Example 3 is sprayed on, first for 2 hours at a spraying rate of 20 kg/h, then at 24 kg/h and a spray pressure of 0.8 bar. The suspension is stirred constantly. The temperature of the air supplied is at most 75° C. The amount of air supplied is about 1900 m$^3$/h.

Then the pellets are dried in the horizontal pan (5 revolutions per minute) at an air inflow temperature of at least 30° C., at most 50° C., and an air inflow amount of 500 m$^3$/h over a period of about 1 to 2 hours.

The dried pellets are then passed through a vibrating screen with a mesh size of 1.6 mm and stored in containers with desiccants until needed for further processing.

| Component | [mg] per capsule | [mg] per capsule |
|---|---|---|
| Dabigatran etexilate methanesulfonate | 86.48[1] | 126.83[2] |
| Acacia (gum arabicum) | 4.43 | 6.50 |
| Tartaric acid | 88.56 | 129.9 |
| Hydroxymethylpropylcellulose 2910 | 2.23 | 3.27 |
| Dimethylpolysiloxane 350 | 0.04 | 0.06 |
| Talc | 17.16 | 25.16 |
| Hydroxypropylcellulose | 17.30 | 25.37 |
| HPMC-capsule | 60[3] | 70[4] |
| Total | 276.2 | 387.1 |

[1]equals 75 mg free dabigatran etexilate
[2]equals 110 mg free dabigatran etexilate
[3]Weight of the capsule approx. 60 mg
[4]Weight of the capsule approx. 70 mg Particularly preferred embodiments of the invention, although already mentioned hereinbefore, are summarized one more time below.

The invention relates to method for preventing stroke in a patient suffering from atrial fibrillation, wherein the patient has at least one risk factors for major bleeding events, the method comprising administering to the patient 110 mg b.i.d. of dabigatran etexilate, optionally in the form of a pharmaceutically acceptable salt thereof. Particularly preferred the method comprises the administration of 110 mg b.i.d, of dabigatran etexilate in the form of the pharmaceutical composition disclosed hereinbefore by way of example.

The invention furthermore relates to the use of dabigatran etexilate, optionally in the form of a pharmaceutically acceptable salt thereof, for the manufacture of a medicament for the prevention of stroke in patients suffering from atrial fibrillation wherein the patient has at least one risk factors for major bleeding events, wherein the use comprises the b.i.d. administration of 110 mg of dabigatran etexilate, optionally in the form of a pharmaceutically acceptable salt thereof. Particularly preferred the use comprises the administration of 110 mg b.i.d. of dabigatran etexilate in the form of the pharmaceutical composition disclosed hereinbefore by way of example.

The invention relates as well to a medicament for the prevention of stroke in a patient suffering from atrial fibrillation wherein the patient has at least one risk factors for major bleeding events, the medicament comprising 110 mg of dabigatran etexilate, optionally in the form of a pharmaceutically acceptable salt thereof. Particularly preferred, the medicament is adapted for b.i.d. administration. Particularly preferred the medicament comprises the administration of 110 mg b.i.d. of dabigatran etexilate in the form of the pharmaceutical composition disclosed hereinbefore by way of example.

I claim:

1. A method for preventing stroke in a patient suffering from atrial fibrillation, wherein the patient has at least one risk factor for major bleeding events, the method comprising administering to the patient 110 mg b.i.d. (twice daily) of dabigatran etexilate, optionally in the form of a pharmaceutically acceptable salt thereof, and wherein the risk factor for major bleeding events includes reduced creatinine clearance of 30 mL/min or less.

2. The method according to claim 1, wherein the patient has at least two risk factors for major bleeding events.

3. The method according to claim 2, wherein a further risk factor for major bleeding events includes an age of 75 years or greater.

4. The method according to claim 2, wherein a further risk factor for major bleeding events includes a history of earlier bleeding events.

5. A method for preventing stroke in a patient with atrial fibrillation and has a reduced creatinine clearance of 30 mL/min or less, the method comprising administering 110 mg b.i.d. of dabigatran etexilate, optionally in the form of a pharmaceutically acceptable salt thereof, to the patient and modifying the administration as necessary to maintain plasma levels of dabigatran in the patient between about 20 ng/mL to about 180 ng/mL, wherein the patient is at a reduced risk for a major bleeding event when compared to conventional warfarin therapy.

6. The method according to claim 5, wherein the plasma levels of dabigatran are between about 43 ng/mL to about 143 ng/mL.

7. The method according to claim 5, wherein the plasma levels of dabigatran are between about 50 ng/mL to about 120 ng/mL.

8. The method according to claim 5, wherein the plasma levels of dabigatran are between about 50 ng/mL to about 70 ng/mL.

9. The method according to claim 5, wherein the plasma levels of dabigatran are between about 60 ng/mL to about 100 ng/mL.

10. The method according to claim 5, wherein the major bleeding event is a life-threatening bleeding event.

11. The method according to claim 5, wherein the plasma levels of dabigatran is determined using the standardized lyophilized dabigatran method.

12. The method according to claim 1 or 5, wherein the dabigatran etexilate, optionally in the form of a pharmaceutically acceptable salt thereof, is co-administered with an antiplatelet agent.

13. The method according to claim 12, wherein the antiplatelet agent is aspirin and is administered at less than or equal to 100 mg per day.

14. The method according to claim 12, wherein the antiplatelet agent is aspirin, dipyridamole, clopidogrel, abciximab, eptifibatide, tirofiban, epoprostenol, streptokinase, or a plasminogen activator.

15. The method according to claim 1 or 5, wherein the dabigatran etexilate, optionally in the form of a pharmaceutically acceptable salt thereof, is co-administered with an antiarrhythmic agent.

16. The method according to claim 15, wherein the antiarrhythmic agent is a potassium channel blocker, sodium channel blocker, beta blocker, or calcium channel blocker.

17. The method according to claim 15, wherein the antiarrhythmic agent is quinidine, procainamide, disopyramide, lidocaine, mexiletine, tocainide, phenytoin, flecainide, encainide, propafenone, moracizine, propranolol, esmolol, metoprolol, timolol, atenolol, miodarone, sotalol, dofetilide, ibutilide, erapamil, diltiazem, amiodarone, bretylium, verapamil, diltiazem, adenosine, or digoxin.

18. The method according to claim 17, wherein the antiarrhythmic agent is quinidine.

* * * * *